US009567576B2

(12) United States Patent
Lee et al.

(10) Patent No.: US 9,567,576 B2
(45) Date of Patent: Feb. 14, 2017

(54) STRAIN EXPRESSING FRSA AND METHOD FOR PRODUCING ETHANOL USING SAME

(71) Applicant: SOGANG UNIVERSITY RESEARCH FOUNDATION, Seoul (KR)

(72) Inventors: Kyung-Jo Lee, Seoul (KR); Yu Ra Kim, Seoul (KR); Jung Kee Lee, Daejeon (KR); Sun-Shin Cha, Gyeonggi-do (KR); Kyu-Ho Lee, Seoul (KR)

(73) Assignee: SOGANG UNIVERSITY RESEARCH FOUNDATION, Seoul (KR)

( * ) Notice: Subject to any disclaimer, the term of this patent is extended or adjusted under 35 U.S.C. 154(b) by 0 days.

(21) Appl. No.: 14/439,317

(22) PCT Filed: Oct. 18, 2013

(86) PCT No.: PCT/KR2013/009311

§ 371 (c)(1),
(2) Date: Apr. 29, 2015

(87) PCT Pub. No.: WO2014/069823

PCT Pub. Date: May 8, 2014

(65) Prior Publication Data

US 2015/0299686 A1 Oct. 22, 2015

(30) Foreign Application Priority Data

Oct. 29, 2012 (KR) ........................ 10-2012-0120128
Nov. 16, 2012 (KR) ........................ 10-2012-0129937

(51) Int. Cl.

| | |
|---|---|
| ***C12N 9/88*** | (2006.01) |
| ***C12N 15/09*** | (2006.01) |
| ***C12N 1/21*** | (2006.01) |
| ***C12P 7/06*** | (2006.01) |

(52) U.S. Cl.

CPC ................. *C12N 9/88* (2013.01); *C12P 7/065* (2013.01); *C12Y 301/00* (2013.01); *C12Y 401/01001* (2013.01); *Y02E 50/17* (2013.01); *Y02P 20/52* (2015.11)

(58) Field of Classification Search

None
See application file for complete search history.

(56) References Cited

U.S. PATENT DOCUMENTS

2009/0155871 A1 6/2009 Fu et al.

FOREIGN PATENT DOCUMENTS

| | | | |
|---|---|---|---|
| KR | 10-2011-0007981 A | | 1/2011 |
| KR | 10-2012-0082141 A | | 7/2012 |
| KR | 10-2012-0126827 A | * | 11/2012 |

OTHER PUBLICATIONS

Lee et al., Supplementary Information for Nat. Chem. Bio. doi:10.1038/nchembio.589; published online 2011, 28 pages.*
Sang, H., Mechanisms of Development 121:1179-1186, 2004.*
Machine translation of KR 10-2012-0126827 A, obtained from http://kposd.kipo.go.kr:8088/kiponet/up/kpion/patent/biblio/selectLstPatentBiblio.do on Jun. 15, 2016, 21 pages.*
Lee et al., Nat. Chem. Biol. 7:434-436, 2011.*
Alterthum et al., Appl. Environ. Microbiol. 55:1943-1948, 1989.*
GenBank Database Accession No. CP002469, Nov. 2011, 2 pages.*
"The Encyclopedia of Molecular Biology", Ed. J. Kendrew, Cambridge, Massachusetts, 1994, p. 1091.*
Dien et al., "Bacteria engineered for fuel ethanol production: current status", Appl Microbiol Biotechnol, vol. 63, pp. 258-266, (2003).
Koo et al., "A Novel Fermentation/Respiration Switch Protein Regulated by Enzyme IIAGlc in *Escherichia coli* ", The Journal of Biological Chemistry, vol. 279, No. 30, pp. 31613-31621, (2004).
Lin et al., "Ethanol fermentation from biomass resources: current state and prospects", Appl Microbiol Biotechnol, vol. 69, pp. 627-642, (2006).

* cited by examiner

*Primary Examiner* — David J Steadman
(74) *Attorney, Agent, or Firm* — Vorys, Sater, Seymour & Pease LLP; Mih Suhn Koh

(57) ABSTRACT

The present application relates to a strain expressing the FrsA protein, and a method for producing ethanol using the same. The FrsA of the present application has a high PDC enzyme activity for a pyruvate, which is a substrate, and thus can be used in a process for producing ethanol. In addition, an FrsA mutant having improved stability in a host cell can be more effective in producing ethanol due to the increase in stability when the FrsA mutant is overexpressed together with $IIA^{Glc}$, compared with when using conventional *Zymomonas mobilis*-derived PDC.

4 Claims, 18 Drawing Sheets

FIG. 5

```
        1                                                    50 53
V. v  ---MSEEVSENLSSTLFVKHKQAKETSALTQYMPTSQ--SLLDEIKEPNGESWYKNLSRLQWVWQSVDP
V. p  ---MSEEVSKHLSETLEANHRQAKETSELTRYMPSSQ---SFLDEKREEDGYNWTRNLRRMQWTWQGLDP
V. c  ---MSEASSENLSSTLPQNHKQAKETSSLTQYMPSSL--ELLDTRREQSSQAWYKNLSRLQWIWQSVDP
E. c  -------MTQASLSETLEKPRPNHPETSTLVRRFNHGAQPPVQSALDGKTIPHWYRMINRLMWIWRGIDP
S. f  -------MTQANLSKTLFKPRFKHPETSTLVRRENHGAQPPVQSALDGKTIPHWYREINRLMWIWRGIDP
S. e  ------MTQARLSETLEKPRPKHTETSTLVRRFNRGSQPEMQSALDGKKVPHWYRMINRLMWIWRGVDP
Y. p  MEATVTMAQANLSKTLFKPRFKHPETSTLVPRTHCNHVVNIHSALDGDTANHWYRMINRLMWTWRGIDP

                                         100
V. v  IEQEQVLARIASSKHSRTDEQWLDTVMGYHSGNWAYEWTRLGMEHQKRAGEMTNEA-RSEALESASLCY
V. p  IEIEAVLARIAASKHSRTHEEWLDTVMGYHSGNWTYEWTKLGMLHQKRSSQLKGEE-AADELFNASLCF
V. c  VEQEEILARIASSKHSRTHDEWLDTVMGYRSGNWTYEWTRVGMLHQKQAAERQGEE-RADQMETAALYY
E. c  REILDVQARIVMSDAERTDDDLYDTVIGYRGGNWIYEWATQAMVWQQKSCAEDDPQLSGRHWLHAATLY
S. f  REILDVQARIVMSDAERTDDDLYDTVIGYRGGNWIYEWATQAMVWQQKACTEEDPQLSGRHWLHAATLY
S. e  REILDVQARIVMSDAERTDEDLYDTVIGYRGGNWIYEWASKQAMDWQQKRCQEQDAMRSGRYWLHASTLY
Y. p  LEIEEVLSRIACSKAEHSNNELLDTVVGYRNGNWIYEWANQGMMWQQKAMEETDPGESSQEWLNAANLY

                     150
V. v  SIAGYPHLKEDNLAIQAQVLSNSAYLEAAKKSKYIINQLEIPFEKG-KITAHLHLT-NTDKPHPVVIVS
V. p  SIAGYPHLKNDNLATQAQVLASSAYTEATEKTKYIVKRLEIPYQKK-SIIAHLHLT-STEKPQPVVLVS
V. c  SIAGYPHLPNDNLALQAQVLANNAYQEAAKLTGEVVKRLEFSYQNK-KIAGYLHLA-NTDSPKPVVLVS
E. c  NIAAYPHLKGDDLAEQAQALSNRAYEEAAQRLPGTMRQMEFTVPGGAPITGFLHMP-KGDGPFPTVLMC
S. f  NIAAYPHLKGDDLAEQAQALSNRAYEEAAQRLPGTMRQMEFTVPGGAPITGFLHMP-KGDGPFPTVLMC
S. e  NIAAYPHLKGDELAEQAQALANRAYEEAAQRLPGSLREMEEAVPGGSPVTAFLHMP-KGDGPFPTVLMC
Y. p  SIASYPHLKGDELSEQAEVLSNRAYEEAAKYLPYTLKEVTFPISDGGSLSGFLHMPTVGSAPFPTVLMC

  200  203                                                250
V. v  AGLDSLQTLMWRLERDHLAKHDIAMLTVDMPSVGYSSKYPLTEDYSRLHQAVLNELFSIPYVDHHRVGL
V. p  AGLDSLQTDLWTVFRDHLAKINIAMLTVDMPSIGHNTHWNLTEDTSVLHQAVLNELYSIPWVDHHRVGL
V. c  AGLDSLQTLMWRLERDYLAKRDIAMLTIDMPSLGASSRWPLTEDSSCLHQAVLNQLADLPWVDHFRIGL
E. c  GGLDAMQTDYYSLYERYFAPRGIAMLTIDMPSVGFSSKWKLTQDSSLLHQHVLKALPNVPWVDHTRVAA
S. f  GGLDAMQTDYYSLYERYFAPRGIAMLTIDMPSVGFSSKWKLTQDSSLLHQHVLKALPNVPWVDHTRVAA
S. e  GGLDAMQTDYYTLYERYFAPRGIAMLTLDMPSVGFSSKWKLTQDSSLLHQHVLKALPNVPWVDHTRVAA
Y. p  GGLDTLQSDYHRLFRDYLEPKGIAMLTIDLPSVGASSRWKLTQDTSYLHQQVLQALADVPWVDHQRVSV

        272                         300
V. v  IGFRFGGNAMVRLSFLEQEKIKACVILGAPIHDIFASPQKLQQMPKMYLDVLASRLGKSVVDIYSLSGQ
V. p  IGFRFGGNAMVRLSFLEQDKINACVSMGAPIHDVLSSPDKLKSHPKMYLDVLASRLGKNAVDIHSLSGQ
V. c  IGFRFGGNAMARLAFLESDKVKACVSLGAPIHDIFTSPNKLAAMPKMYLDVLASRLGKNVVDVRSLSGQ
E. c  FGFRFGANVAVRLAYLESPRLKAVACLGPVVHTLLSDFKCQQQVPEMYLDVLASRLGMHDASDEALRVE
S. f  FGFRFGANVAVRLAYLESPRLKAVACLGPVVHTLLSDFKCQQQVPEMYLDVLASRLGMHDASDEALRVE
S. e  FGFRFGANVAVRLAYLEAPRLKAVACLGPVVHALLSDPQRQITVPEMYLDVLASRLGMHDASDEALRVE
Y. p  FGFRFGANVAVRLGYLEPQRVRAVACLGPIVHRLLCNSDSLRKVPDMYMDVMASRLGMADSTDETLNTE

              350                                                400
V. v  SAAWSLKVQSELESRRETKVPILANSLEGDPVSPYSDNQSVAFFSTYGKAKKISSKTITQSYEQSLDLAINWLSDELLK
V. p  LMAWSLKVQGILSSERTPVPILAMSLEGDPVSPYSIMQMVALYSDYGKAKKISAKTITQGYEQSLDLAIKWLEDELME
V. c  LMAWSLKVQSFMSGRKTKTPILALGLEGDPVSPYSDNQLVALFSQGGQAKKVKSKTISQSYEQCLDLAINWLSDELCK
E. c  LNRYSLKVQGLLG-RRCPTPNLSGYWNDDPSCPEEDCRLITCSSADGKLLESPSPVYRNSDKGLQEITDWTCKRLC-
S. f  LNRYSLKVQGLLG-RRCPTPNLSGYWNDDPSPEEDSRLITSSSAHGKLLESPSPVYRNSDKGLQEITGWIEKRLC-
S. e  LNRYSLKVQGLLG-RRCSTPNLSGFWNDDPSCPEESCRLITTSSDGKLLESPSPVYRNSDHALQEITDWTSHRLC-
Y. p  SNRYSLKTQSLLG-RRCQTPSLAGFWSNDPSPRESAKLICSSSAIGKLLAYPSKPLYENSHAALIQTSEWLSDKMR-
```

| | NCBI accession number | |
|---|---|---|
| *V. vulnificus* | AA008857 | SEQ ID NO: 2 |
| *V. parahaemolyticus* | EED26191 | SEQ ID NO: 37 |
| *V. cholerae* | NP_231907 | SEQ ID NO: 38 |
| *E. coli* | AP_000892 | SEQ ID NO: 39 |
| *S. flexneri* | NP_706239 | SEQ ID NO: 40 |
| *S. enterica* | YP_001571692 | SEQ ID NO: 41 |
| *Y. pestis* | AAM84545 | SEQ ID NO: 42 |

FIG. 8B

```
Wt-FrsA    MSEEVSKNLSETLFVKHKQAIETSALTQYMPTSQSLLDEIKEKNGFSWYRNLRRLQWVWQ
FrsA_mt    ------------------MAIETSALTQYMPTSQSLLDEIKEKNGFSWYRNLRRLQWVWQ
                             ******************************************

Wt-FrsA    GVDPIEQEQVLARIASSKHSRTDEQWLDTVMGYHSGNWAYEWTRLGMEHQKRAGEMTNEA
FrsA_mt    GVDPIEQEQVLARIASSKHSRTDEQWLDTVMGYHSGNWAYEWTRLGMEHQKRAGEMTNEA
           ************************************************************

Wt-FrsA    ASEALFSASLCYSIAGYPHLKSDNLAIQAQVLANSAYLEAAKKSKYIIKQLEIPFEKGKI
FrsA_mt    ASEALFSASLAYSIAGYPHLKSDNLAIQAQVLANSAYLEAAKKSKYIIKQLEIPFEKGKI
           ********** *************************************************

Wt-FrsA    TAHLHLTNTDKPHPVVIVSAGLDSLQTDMWRLFRDHLAKHDIAMLTVDMPSVGYSSKYPL
FrsA_mt    TAHLHLTNTDKPHPVVIVSAGLDSLQTDMWRLFRDHLAKHDIAMLTVDMPSVGYSSKYPL
           ************************************************************

Wt-FrsA    TEDYSRLHQAVLNELFSIPYVDHHRVGLIGFRFGGNAMVRLSFLEQERIKACVILGAPIH
FrsA_mt    TEDYSRLHQAVLNELFSIPYVDHHRVGLIGFRFGGNAMVRLSFLEQERIKACVILGAPIH
           ************************************************************

Wt-FrsA    DIFASPQKLQQMPKMYLDVLASRLGKSVVDIYSLSGQMAAWSLKVQGFLSSRKTKVPILA
FrsA_mt    DIFASPQKLQQMPKMYLDVLASRLGKSVVDIYSLSGQMAAWSLKVQGFLSSRKTKVPILA
           ************************************************************

Wt-FrsA    MSLEGDPVSPYSDNQMVAFFSTYGKAKKISSKTITQGYEQSLDLAIKWLEDELLR
FrsA_mt    MSLEGDPVSPYSDNQMVAFFSTYGKAKKISSKTITQGYEQSLDLAIKWLEDELLR
           *******************************************************
```

Wt-FrsA SEQ ID NO : 2

FrsA_mt SEQ ID NO : 8

STRAIN EXPRESSING FRSA AND METHOD FOR PRODUCING ETHANOL USING SAME

CROSS-REFERENCE TO RELATED APPLICATIONS

The present application is a national stage application of International Patent Application No. PCT/KR2013/009311, filed Oct. 18, 2013, and claims the benefit of Korean Patent Application Nos. 2012-0120128, and 2012-0129937, filed Oct. 29, 2012 and Nov. 16, 2012, respectively in the Korean Intellectual Property Office, the disclosure of which are incorporated herein.

STATEMENT OF SEQUENCE LISTING

The Sequence Listing submitted in text format (.txt) filed on Jun. 29, 2015, named "SequenceListing.txt", created on Jun. 10, 2015, 42.8 KB), is incorporated herein by reference.

BACKGROUND OF INVENTION

Field of the Invention

The present disclosure generally relates to a microorganism expressing FrsA protein or mutant form thereof and methods of producing ethanol using the same.

Description of the Related Art

Efforts to reduce heavy reliance on foreign oil as well as environmental damages have led to efforts to find alternative energy sources. One of them is to produce bioethanol from biomass.

However, the progression of bioethanol production has been hampered due to its low efficiency and high cost of production. Thus there are needs to improve the process to increase the economics and to lower investment risk. The efforts are generally focused on the development of a conversion process to change the biomass into materials so that it can be utilized by microorganisms as a glucose source; and on the development and improvement of enzymes involved in the glucose metabolism in cells.

In the process for producing bioethanol using microorganisms such as *Saccharomyces cerevisiae, Zymomonas mobilis* or *Escherichia coli* and the like, sugars such as hexose or pentose are fermented to produce bioethanol.

Theses microorganisms are often genetically modified to express exogenous enzymes to improve the efficiency of ethanol production. Such exogenous enzymes are represented by pyruvate decarboxylase (PDC) and alcohol dehydrogenase (ADH). When *E. coli* are used as a host cell, PDC and ADH derived from *Zymomonas mobilis* have been utilized to convert pyruvates to ethanol.

These enzymes have capabilities to increase the efficiency of the ethanol production thus reducing the amount of biomass used in the process. Therefore modification of the enzymes to improve their activity plays a major role in reducing the total cost of the process.

US Patent Publication No. 2009/0155871 discloses a construct having a photo responsive promoter and genes encoding PDC and ADH from *Zymomonas mobilis* and methods to produce ethanol using cyanobacteria transformed with the same.

KR Patent Publication No. 2011-0007981 discloses a novel ADH and methods for producing ethanol using a microorganism transformed with the same.

KR Patent Publication No. 2012-0082141 discloses a method to produce ethanol using the strain which has been modified to reduce its glycerol production and transformed with ADH and PDC from *Saccharomyces cerevisiae.*

However, there are no reports using FrsA from *Vibrio vulnificus* as PDC to improve the ethanol production in cells and there are needs to develop new strains which are able to produce ethanol.

SUMMARY OF THE INVENTION

The present disclosure is based on the characterization of wild type and mutant form of FrsA proteins and genes involved in the sugar metabolism and its use in ethanol production.

In one aspect, the present disclosure provides a cell transformed with a FrsA gene or mutant FrsA or biologically equivalent forms thereof In one embodiment, the gene contained in the cell is represented by SEQ ID Nos: 1, 5 or 7.

In other embodiment, the cell which may be transformed with the present genes includes a bacterium or a yeast in which the bacteria is selected from the group consisting of *Escherichia coli, Corynebacterium glutamicum, Erwinia chrysanthemi, Zymomonas mobilis, Klebsiella* spp., *Bacillus stearothrermophilus, Kluveromyces* spp., *Pachysolen tanophilus, Clostridium* spp. and *Candida shehatae*; and the yeast is *Saccharomyces seravisiae* or *Pichia stipitis.*

In one embodiment, the bacterium is further transformed with an alcohol dehydrogenase gene.

In other embodiment, the cell is further transformed with a $IIA^{Glc}$ gene.

In other embodiment, the $IIA^{Glc}$ gene is represented by SEQ ID NO: 3.

In other aspect, the present disclosure provides mutant FrsA proteins represented by SEQ ID NO: 2 in which the amino acid residue 131 is substituted from cysteine to alanine, or the amino acid residues from 2 to 19 are deleted and the amino acid residue 131 is substituted from cysteine to alanine.

In other aspect, the present disclosure provides an isolated polynucleotide encoding the protein of the present disclosure.

In one embodiment, the polynucleotide is represented by SEQ ID NOs: 5 or 7.

In other aspect, the present disclosure provides a vector comprising the polynucleotide according to the present disclosure.

In other aspect, the present disclosure provides a microorganism comprising the vector according to the present disclosure.

In other aspect, the present disclosure provides a method for producing bioethanol using the microorganism according to the present disclosure.

In one embodiment, the present method further comprises steps of contacting the microorganism with a carbon source and culturing the microorganism in a condition for fermentation.

In other embodiment, the carbon source which may be used for the present method is selected from the group consisting of a starch, a cellulose, a hemi-cellulose, a pentose and a hexose.

In other embodiment, the carbon source which may be used for the present method is selected from the group consisting of a lactose, a glucose, a xylose, an arabinose, a galactose and a mannose.

In other embodiment, the microorganism which may be transformed with the present genes or vectors is *E. coli* or *Corynebacterium glutamicum.*

In still other embodiment, the fermentation condition is controlled by controlling the availability of oxygen and/or the pH.

In still other embodiment, the method is performed under an anaerobic or facultative anaerobic condition.

The foregoing summary is illustrative only and is not intended to be in any way limiting. Additional aspects and/or advantages of the invention will be set forth in part in the description which follows and, in part, will be obvious from the description, or may be learned by practice of the invention.

Advantageous Effects

FrsA or its mutants from *V. vulnificus* of the present disclosure has a high PDC activity for the substrate pyruvate and thus can be advantageously used for producing ethanol. Also the mutant forms of FrsA having a high stability in cells have an ethanol productivity in cells which is much higher than PDC from *Zymomonas mobilis* particularly together with $IIA^{Glc}$. Thus the present FrsA and its mutant forms as disclosed herein can be advantageously used for the bio-ethanol production.

BRIEF DESCRIPTION OF THE DRAWINGS

These and/or other aspects and advantages of the invention will become apparent and more readily appreciated from the following description of the embodiments, taken in conjunction with the accompanying drawings of which:

FIG. 5 is an alignment of amino acid sequences of FrsA *V. vulnificus* (V. v) with its orthologs. *V. vulnificus* (V. v) FrsA sequence was aligned with orthologs as disclosed in GenBank as indicated below using the program ClustalW. The residues of identical and similar amino acids are marked with blue asterisk and the green dots, respectively. Three catalytic residues (R53, D203, and 8272) are indicated as red letters Amino acid sequences were obtained from NCBI Database: V. v (*Vibrio vulnificus* NP_759330.1); V. p (*Vibrio parahaemolyticus* EED26191); V. c (*Vibrio cholerae* NP_231907); E. c (*Escherichia coli* AP_000892); S. f (*Shigella flexneri* NP_706239); S. e (*Salmonella enterica* YP_001571692); and Y. p (*Yersinia pestis* AAM84545).

FIG. 8B is an alignment of amino acid sequences of wild-type FrsA with mutant FrsA[mt]. The mutant FrsA comprises an amino acid deletion (residues 2 to 19 from N-terminal) and a substitution of cysteine to alanine at residue 131. Mutagenized residues are indicated as red letters.

DETAILED DESCRIPTION OF THE EMBODIMENTS

Figure 1A:
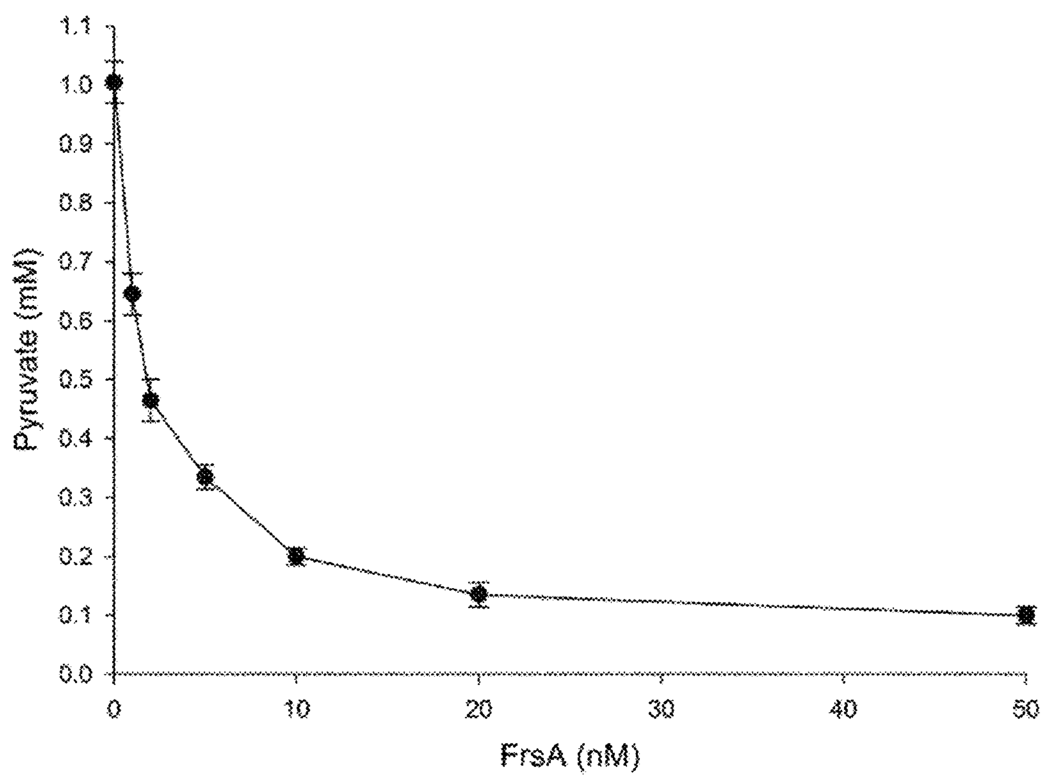
FIG. 1A is a graph showing the enzymatic activity of recombinant FrsA according to one embodiment of the present disclosure on the decomposition of pyruvate. One mM of pyruvate was added to reaction mixtures containing various concentrations of FrsA from 0 to 50 nM and incubated for 5 min. Then the amount of pyruvate remained was measured and the data represents an average of three independent experiments.

In the present disclosure, the biochemical properties of FrsA were characterized. Glucoses are catabolized to pyruvates during the metabolism. At this point FrsA (Fermentation Respiration Switch) protein functions as a switch at the branch point between respiration and fermentation to direct the metabolism to fermentation In the present disclosure, it was found that FrsA catalyzes the decarboxylation reaction of pyruvates without the help of a cofactor. Also it was found that IIA$^{Glc}$ protein increases the activity of FrsA protein.

Also found in the present disclosure is that the ethanol productivity by a host can be increased by overexpressing FrsA and/or IIA$^{Glc}$.

Further it was found in the present disclosure that the ethanol productivity by a host can be further improved by using mutant FrsA and IIA$^{Glc}$ and overexpressing the same in a host.

Thus in one aspect, the present disclosure provides an isolated FrsA gene and protein as well as its mutant forms. Encompassed in the present disclosure are wild-type FrsA gene and protein as well as biological equivalents thereof. The variation at the nucleic acid sequence may be or not be accompanied by amino acid changes. When the changes occur at the amino acid level, a variety of amino acid variants are included in the present disclosure as long as they are biologically equivalent to FrsA according to the present disclosure. In one embodiment the gene and protein are derived from *Vibrio vulnificus*. In other embodiment, the gene and protein are each represented by SEQ ID Nos: 1 and 2, respectively. Also encompassed in the present disclosure are sequence variants at a nucleic acid and amino acid level having substitutions therein as long as they are biologically equivalent thereto. In one embodiment, the variant is a mutant FrsA having an amino acid sequence of SEQ ID NO; 2 in which the cysteine at amino residue 131 is changed to alanine and a mutant frsA gene encoding the same. The mutant frsA gene and protein in which cysteine at residue 131 is changed to alanine are represented by SEQ ID NOs: 5 and 6, respectively.

In one embodiment, the nucleic acid sequence encoding the protein of SEQ ID NO.2 is represented by SEQ ID NO. 1. But the sequence is not limited thereto. Due to the degeneracy of the codon encoding the amino acid, one amino acid sequence is represented by more than one nucleic acid sequences, which are also encompassed in the present disclosure.

Further the present disclosure provides a cell or a microorganism transformed with frsA gene from *V. vulnificus*. In one embodiment, frsA gene is represented by SEQ ID NO: 1. In other embodiment, frsA gene is represented by a nucleotide sequence encoding FrsA protein represented by SEQ ID NO: 2 in which the cysteine residue at 131 is substituted with alanine and/or residues 2-19 from the N-terminal are deleted.

The cells of the present disclosure which are transformed with a frsA gene or biological equivalent thereof including mutant frsA genes as described herein express FrsA protein and the amount and/or the time of the protein expression may be controlled as desired by for example use of an appropriate promoter known in the art.

The cells may be further transformed with an ADH (Alcohol dehydrogenase) gene and/or IIA$^{Glc}$ gene.

ADH genes which may be employed for the present disclosure may come from various origins. For example, in one embodiment ADH genes from *S. cerevisiae* having GenBank Accession NOs: NM_001183340, NM_001182812, or NM_001181122 may be included in the present disclosure without being limited thereto.

IIA$^{Glc}$ protein encoded by crr gene is a glucose-specific transporter. This protein is capable of regulating the activity of a target protein by binding to the target. It was found in the present disclosure that one of its targets is FrsA protein and IIA$^{Glc}$ protein can increase the activity of FrsA by about 2 times when the cells were transformed with IIA$^{Glc}$ in addition to FrsA.

ADH and/or IIA$^{Glc}$ may be used in the present disclosure to facilitate the activity of FrsA by being transformed into appropriate cells as described herein.

In the present disclosure, for the production of ethanol, frsA genes may be transformed into host cells or microorganisms such as bacteria or yeast cells which are able to utilize as a carbon source various substrates including a hexose, a pentose and lactose.

In one embodiment, microorganisms or cells which may be cultivated in an anaerobic or facultative anaerobic condition are used. Anaerobic microorganisms can grow in the absence of oxygen and their growth is inhibited by the presence of oxygen. The facultative anaerobic microorganisms usually need oxygen for respiration; however are able to grow also in the absence of oxygen.

Examples of facultative anaerobic microorganisms include *Escherichia coli, Corynebacterium glutamicum, Erwinia chrysanthemi, Zymomonas mobilis, Klebsiella* spp, *Bacillus stearothrermophilus, Kluveromyces* spp., *Pachysolen tanophilus*, lactic acid bacteria, *Clostridium* spp., and *Candida shehatae* as bacterial cells, and include *Saccharomyces seravisiae*, and *Pichia stipites* as yeast cells, without being limited thereto.

Cells or microorganisms which also may be used for the present disclosure include Archaea *Euryarchaeota, Hyperthermophiles, Thermococcus* spp. *Pyrococcus* spp., and *Thermococcus onnurineus* NA1. Lactic acid bacteria may be used for the present disclosure include *Streptococcus* spp., *Lactobacillus* spp., *Lactococcus* spp., and *Leuconostoc* spp.

The cells or microorganisms which are employed in the present disclosure for the ethanol production have to meet some requirements such as a particular ranges of temperature for growth, a particular ranges of pH for growth, resistance to alcohol, resistance to osmotic pressure, a certain growth rate, a certain productivity to for example a certain substrate, a certain efficiency of production, genetic stability and resistance to inhibitors. Suitable cells may be selected by ordinary person in the art as desired. In one embodiment, *S. cerevisiae, E. coli*, or *Zymomonas mobilis* is used. In other embodiment, *Thermococcus onnurineus* NA1 is used. In still other embodiment, *Corynebacterium glutamicum* is used.

Methods and vectors to introduce a frsA gene to cells are known in the art. For example, a nucleotide sequence encoding FrsA protein is obtained by an appropriate method such as PCR, the product of which is then cloned into an appropriate vector conventionally used for protein expression such as pQE30, pGEM-T®, pSC101, ColE1, pBR322, pUC8/9, pHC79, pUC19 or pET. The vectors carrying the gene are then transformed into appropriate cells. For the production of ethanol, FrsA proteins are over expressed in the transformed cells.

The frsA gene in the present disclosure is present in cells as an integrated form into a host genome or as separately from the genome in a plasmid. In one embodiment, the gene is present as integrated in a host genome for stable expression of the protein.

The frsA gene may also be introduced into bacterial cells as a part of an operon. The operon includes a frsA gene and regulatory sequences to control the expression of the frsA gene, in which the regulatory sequences include a promoter, an inducer, an operator and a ribosomal binding site. For examples of such operons, those described in U.S. Pat. No. 5,000,000 may be referred.

The recombinant FrsA proteins expressed may be isolated and purified using methods known in the related art. For example, the cultured transformed cells are ruptured to prepare crude cell extracts, which then may be purified by conventional methods such as a chromatography column.

As described in Table 1 of the present disclosure, the present FrsA shows a Km value similar to PDC from *Zymomonas*; however shows Kcat and Kcat/km values which are eight times higher than that of *Zymomonas*. This indicates the superior catalytic efficiency of the present FrsA. Further the present FrsA has a Kcat and Kcat/km value which are about 19 and about 110 times higher, respectively than that from *S. cerevisiae*.

In other aspect, the present disclosure relates to a method to producing ethanol using the cells transformed with FrsA gene or its mutant as disclosed herein.

Bioethanol is a type of biofuel which is produced by fermenting biomass. The present FrsA and its mutant forms when introduced into cells can advantageously be used for the production of ethanol at high efficiency through the fermentation of sugars.

The cells or microorganisms which may be used for the present methods are as described above. Also the cells may be further transformed with $IIA^{Glc}$ in addition to FrsA as described above. In one embodiment, the present methods include steps of providing cells expressing or carrying FrsA of the present disclosure; contacting the cells with a carbon source; and culturing or incubating the cells under a fermentation condition.

The media, culture condition such as temperatures and types of carbon source and the like may be appropriately selected considering the types of cells utilized from what is known in the art by ordinary person in the art without difficulty. For example Peterson & Ingram et. al. Ann. N.Y. Acad. Sci. 1125: 36372 (2008) may be referred.

For the cells or microorganisms carrying or expressing FrsA are as described hereinbefore.

Carbon sources which may be used for the present method are not particularly limited as long as it can be used for the ethanol production. For example, carbon sources from biomass are used in one embodiment. Biomass refers to biological materials or organic matter derived from living or recently living organisms, which are often plants or plant-based materials.

Biomass mainly consists of two components, i.e., carbohydrates and non-carbohydrates. The carbohydrates are subdivided into a cellulose, i.e., a linear polymer consisting of β-1,4 linked glucose unit; hemi-cellulose, i.e., a complex branched polymer consisting of a β-1,4 linked xylose backbone and branches consisting of arabinose, galactose, mannose and glucuronic acid. The non-carbohydrates are lignins having cross-linked phenylpropanoid structures. In one embodiment, biomass such as lignocelluloses are used and the biomass is pretreated by a process such as described in WO2009/071996 before the biomass is used for the present methods.

Also carbon sources which may be used for the present disclosure include lactose or major sugars present in biomass such as glucose, xylose, arabinose, galactose and mannose without being limited thereto.

The fermentation process may be regulated by controlling the amount of oxygen present and/or the pH. The control of the amount of oxygen, i.e., anaerobic or facultative anaerobic condition and pH may vary depending on the microorganisms employed and for example, Lin et al, Appl Microbiol Biotechnol (2006) 69: 627642 may be referred.

The anaerobic or facultative anaerobic microorganisms which may be employed for the present disclosure include, for example, *Escherichia coli, Corynebacterium glutamicum, Erwinia chrysanthemi, Zymomonas mobilis, Klebsiella* spp, *Bacillus stearothrermophilus, Kluveromyces* spp., *Pachysolen tanophilus*, lactic acid bacteria, *Clostridium* spp., *Candida shehatae* as bacterial cells, and include *Saccharomyces seravisiae*, and *Pichia stipites* as yeast cells, without being limited thereto.

The transformed cells of the present disclosure carrying FrsA or its mutants may be cultured using methods known in the art. Also the cells may be cultivated in various culture methods known in the art such as batch culture, continuous culture, fluid batch culture or reactor culture.

The present disclosure is further explained in more detail with reference to the following examples. These examples, however, should not be interpreted as limiting the scope of the present invention in any manner.

EXAMPLES

Example 1

Expression of Proteins and Purification 1-1. frsA Cloning and Purification

Genomic DNA from *V. vulnificus* (3) was used as template and [FrsAexp-FK (5'-GGGGTACCCCGAATATGTCAGAAGAAGTCAGC-3'(SEQ ID NO: 9); KpnI restriction site is underlined) and FrsAexp-RH (5'-CCCAAGCTTGTCACCTTAAGAGTTCATCTTCCAGC-3' (SEQ ID NO: 10); HindIII restriction site is underlined] are used as primers to amplify a full length frsA gene of 1,255-bp in length.

Then the amplified fragment was digested with KpnI and HindIII and cloned into a vector pQE30 (Qiagen, USA) to obtain pQE-frsA. *E. coli* JM109 (Promega) cells carrying the vector was grown in a medium containing 0.2 mM isothiopropylthio-D-galactoside and FrsA proteins were isolated and purified from the cells using $Ni^{+}$-nitrilotriacetic acid affinity column and size exclusion chromatography (Qiagen) according to the manufacturer's instruction.

For cloning *E. coli* FrsA, primers specific to frsA gene of *E. coli* were used. The primers are as follows: ECFrsAexp-FB (5'-CGGGATCCATGACACAGGCAAACCTGAG-3'

Figure 2:
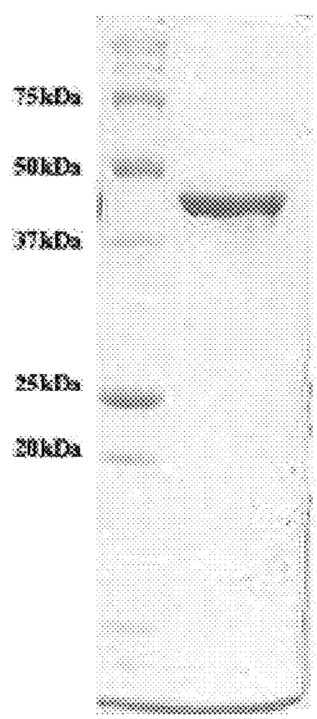
FIG. 2 is a photograph of SDS-PAGE analysis of the purified recombinant FrsA protein

(SEQ ID NO: 11); BamHI restriction site is underlined) and ECFrsAexp-RH: 5'-CCCAAGCTTGCTATCTCCTGTTGT GATGC-3'(SEQ ID NO: 12); HindIII restriction site is underlined). *E. coli* FrsA was prepared as described above Nit nitrilotriacetic acid affinity column and size exclusion chromatography (Qiagen) according to the manufacturer's instruction. The purified proteins were then electrophoresed on a SDS-PAGE gel (Sodium Dodecyl Sulfate-Polyacrylamide) and stained with Coomassie Brilliant blue. As shown in FIG. 2, a protein of 47 kDa in size was confirmed on a gel. To confirm whether FrsAs form a multimer, FrsA proteins were subject to a gel filtration chromatography (Sigma, USA) and the proteins were eluted in 10 mM sodium phosphate buffer (pH 8.0) containing 1 mM DTT and 300 mM NaCl. The estimated molecular weight of FrsA protein is 47 kDa and the results indicate that FrsA proteins are present as a monomer in solution.

1-2. $IIA^{Glc}$ Cloning and Purification

Genomic DNA from *V. vulnificus*(3) was used as template and as primers Crrexp-F (5'-CG GGATCCGACACAATGGGTCTGTTTGAC-3'(SEQ ID NO: 13); BamHI restriction site is underlined) and Crrexp-R (5'-AACTGCAGTAGTAATTACTTAGTTACGCG-'3(SEQ ID NO: 14); PstI restriction site is underlined) are used to amplify crr gene of 522-bp in size encoding full length $IIA^{Glc}$. The amplified products were then digested with BamHI and PstI and cloned into a vector pQE30 to obtain pQE-crr. Phosphorylated and non-phosphorylated recombinant $IIA^{Glc}$ proteins were overexpressed in *E. coli* JM109 in a medium comprising 1.0 mM phophoenolpyruvate or 1.0% glucose, respectively. The expressed proteins were then prepared using $Ni^{+}$-nitrilotriacetic acid affinity column and size exclusion chromatography (Qiagen) according to the manufacturer's instruction as described above.

1-3. Site Directed Mutation in FrsA.

FrsA mutation having alanine at amino acid residue 131 based on SEQ ID NO: 1 instead of cysteine was constructed by overlap-extension method (4) using primers encompassing the mutated region. Nucleotide sequence encoding FrsA having substitution at amino acid residue 131 (C131A) was amplified using two sets of primers as follows: FrsAexp-FK/FrsA FrsA C131AR (5'-GTAACCTGCGATGCTGTAAGCCAAGGATGc-3'(SEQ ID NO: 15))/FrsA C131AF (5'-GCATCCTTGGCTTACAGCATCGCAGGTTAC-3' (SEQ ID NO: 16)). Then the two kinds of PCR products as obtained above were then used a template for the $2^{nd}$ PCR using FrsAexp-FK and FrsAexp-RH as primers represented by SEQ ID Nos: 9 and 10, respectively. Then the amplified products were then digested with KpnI와 HindIII and ligated into pQE30 to obtain pQE-frsAC131A. The constructed plasmid were confirmed by sequencing.

1-4. Preparation of Mutant *V. vulnificus* Having a Deletion in frsA Gene

Genomic DNA of *V. vulnificus* MO624/O30 was used as a template and two primers [frsA-up F (5'-AC ATGCATGCAATAATCGTTTGCGCAGCTCGATA CCC-3'(SEQ ID NO: 17); SphI restriction site is underlined) and frsA-up R (5'-GCTCTAGATCGGCATGTATTGAGTC AATGCCGAGG-3'(SEQ ID NO: 18); XbaI restriction site is underlined)] were used to amplify 838 bp DNA fragment comprising upstream region of frsA. Then the fragment was digested with SphI and XbaI and cloned into pBluescript SK II(+)(Promega) to obtain pSKfrsAup.

1,118-bp DNA fragment comprising downstream of frsA gene prepared by PCR using genomic DNA as a template as described above and the following primers: frsA-downF (5'-GCTCTAGAAGGGGATCCGGTCTCGCCATATTC GGA-3'(SEQ ID NO: 19); XbaI restriction site is underlined) and frsA-downR (5'-GGACTAGTATCCGCTCGAGTGAGCAACATTTGGCC-3'(SEQ ID NO: 20); SpeI restriction site is underlined). The amplified fragment was the digested with SpeI and XbaI and cloned into pSKfrsAup to obtain pSKfrsAup/down, which was then digested with SphI and SpeI to obtain 1,956-bp DNA fragment. The 1,956-bp DNA fragment was then cloned into a suicide vector pDM4(5) to obtain pDM4-frsA. SM10pir strain (6) carrying *E. coli* pDM4-frsA was conjugated with *V. vulnificus* MO624/O30. The successfully conjugated bacteria were selected in thiosulfate citrate bile salt sucrose medium (7). Then the selected colonies were confirmed by PCR using frsA-upF and frsA-downR as primers to confirm the deletion. The strain with frsA deletion was named SM201.

Example 2

Figure 3:
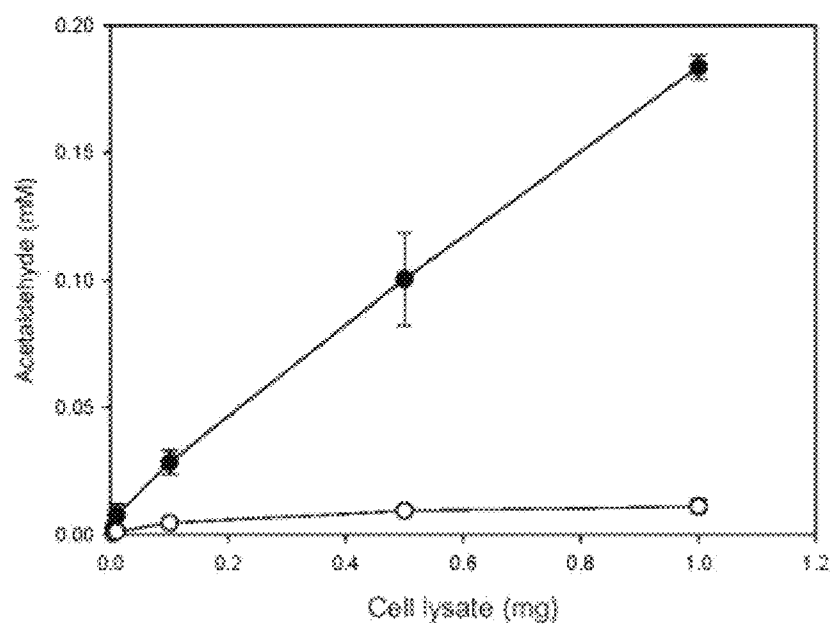
FIG. 3 is a graph showing the concentration of acetaldehyde produced by bacteria expressing wild type FrsA (closed circle) or FrsA defective mutant (open circle).

Biochemical Characterization of FrsA 2-1 Measurement of Reaction Rate Constant FrsA enzymatic analysis was performed in 50 mM sodium phosphate solution (pH 7.0) containing 1 mM DTT and various concentrations of pyruvate. To measure the amount of acetaldehyde produced from pyruvate, 2 mM NADH and 3.7 U of yeast was added to the FrsA reaction mixture (8). Cell lysates from wild-type *E. coli* and frsA mutants (9) were used in the range of 0.005 to 1 mg in amount. The acetaldehyde reaction was initiated by adding FrsA (1 nM) and incubated at 37° C. for 5 min and stopped by adding 50 mM potassium hydrogen phthalate buffer (pH3.0). The residual NADH in the reaction mixture was determined by measuring absorption at 340 nm. For $CO_2$ measurement, FrsA enzyme reaction was performed in 50 mM Tris-HCl buffer (pH 7.0). The amount of carbon dioxide dissolved in the reaction solution was quantified by spectrophotometry after the reaction solution was treated with 10 mM calcium hydroxide (10). Concentrations of the pyruvate and acetaldehyde in the cell lysates and reaction mixtures were determined using Pyruvate Assay Lit (BioVision, USA) and Acetaldehyde UV-method kit (Roche, USA), respectively according to the manufacturer's instruction. To increase the sensitivity of the Acetaldehyde UV-method kit, the reaction mixture was additionally treated with dye (50 ml of 1.0% Tween 20 solution containing 40 mg iodonitrotetrazolium chloride and 10 mg phenazine methosulfate) followed by absorption measurement at 490 nm (11). Results are shown in FIG. 3 and Table 1.

Values of $K_m$ and $K_{cat}$ were calculated as follows. The concentration of reaction products were calculated in the mM unit from the absorption values which were obtained for a total of 1 min for each substrate concentration (S). Then initial reaction rate (Vo) for each concentration of the substrate was determined (here the unit is $mM_{(product)}/sec/mg_{(enzyme)}$). Lineweaver-Burk plot was drawn with the reciprocal values of S and Vo on a X and Y axes, respectively in which case, the reciprocal of X-intercept is $K_m$, and the reciprocal of Y-intercept is $V_{max}$. $K_{eat}$ value expressed in the unit of $sec^{-1}$ was calculated by changing the unit weight of the enzyme to the concentration in mM in the calculated $V_{max}$ ($mM_{(product)}/sec/mg_{(enzyme)}$).

The reaction rates of PDC from *Zymomonas* and yeast were determined in the same way as described for FrsA. Briefly, ADH/NADH coupled assay as described above was performed using a reaction solution MES, pH 6.0 containing 5 mM $MgCl_2$ and 1 mM thiamine pyrophosphate at 25° C. In case of *Zymomonas*, before the reaction was performed, the enzymes were pretreated in a buffer having the following composition (0.1 M sodium citrate buffer, pH 6.0, 20 mM $Mg^{2+}$, 1.5 mM thiamine pyrophosphate) and the reaction was initiated by adding thereto 105 μmol sodium citrate buffer, pH 6.0, 21 μM $MgSO_4$, 18 μM sodium pyruvate, 0.19 μM NADH, 3.7 U yeast alcohol dehydrogenase. The reaction products were analyzed in the same way as described above.

2-3 NMR Spectroscopy 5 mM pyruvate, α-ketoglutarate or α-ketobutyrate was added to a solution (50 mM sodium phosphate and 1 mM dithiothreitol in 95% $D_2O$). Then the reaction mixture was incubated at 20° C. for 90 minutes in the presence or absence of 2 μM FrsA. Then the reaction mixture was kept on ice for 2 hours after which NMR spectroscopy was performed using Bruker DRX500 spectrometer at 500 MHz 의 1H resonance frequency. Results are shown in FIG. 4.

2-4 Enzyme Characteristics of FrsA

A. Activation of Decarboxylation Reaction of Pyruvate by FrsA

Figure 1B:
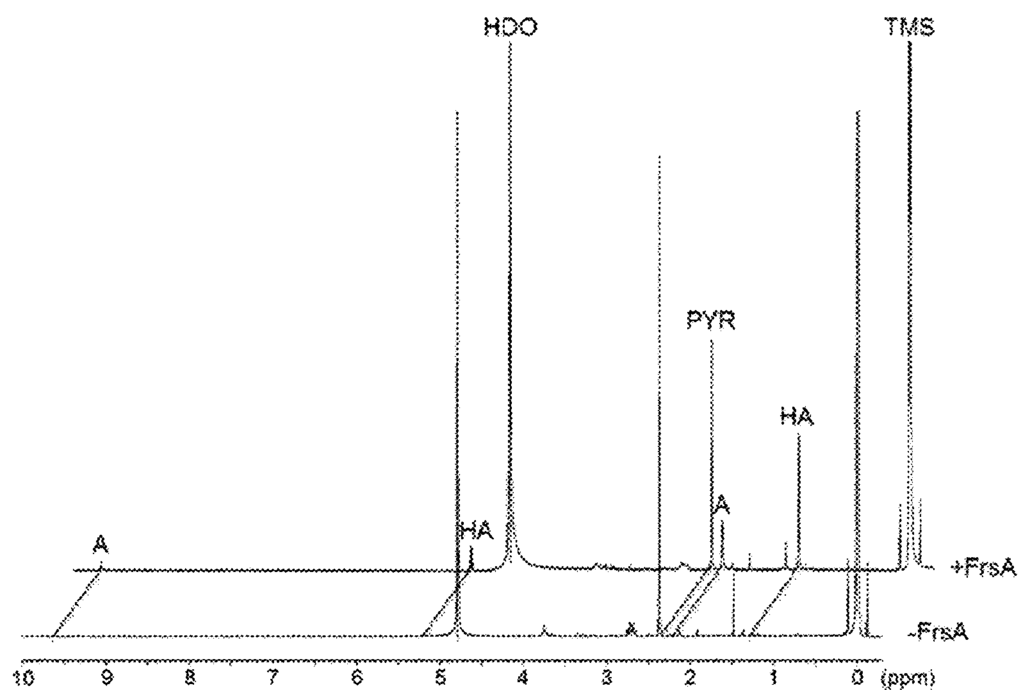
FIG. 1B is a NMR data showing the conversion of pyruvate to acetaldehyde by FrsA. Pyruvate (5 mM) was added to a D2O buffer containing 50 mM sodium phosphate and incubated in the absence or presence of 2 μM FrsA. The reaction mixtures were analyzed by 1H-NMR. The abbreviations are as follows: A, acetaldehyde; AH, hydrated acetaldehyde; PYR, pyruvate; TMS, tetramethylsilane. A standard 1H-NMR spectrum for acetaldehyde is shown in FIG. 4C.
Figure 1C:
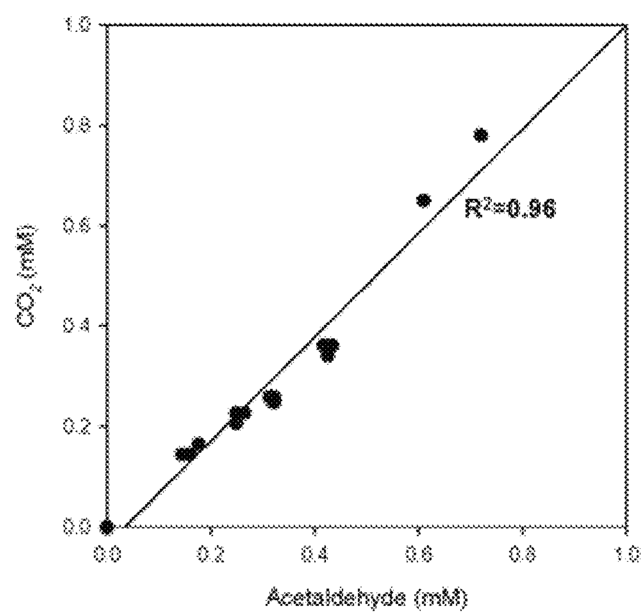
FIG. 1C is a graph showing the concentrations of acetaldehyde and $CO_2$ produced during the FrsA-catalyzed reaction. The concentrations of acetaldehyde and $CO_2$ were measured in reaction mixtures containing 1 nM FrsA and various concentrations of pyruvate ranging from 0 to 1.0 mM. Acetaldehyde and $CO_2$ in each reaction mixture were plotted on the X- and Y-axes, respectively, which was then subjected to a linear regression analysis.

When FrsA as prepared in Example 1 was added to a reaction mixture containing pyruvate, it was found that the concentration of pyruvate was decreased (FIG. 1A). Through the 1H NMR spectroscopy, it was identified that such decrease in the concentration was led to an increase in the concentration of acetaldehyde (FIG. 1B). Consistent results were obtained in the analysis of the reaction mixture containing various concentrations of pyruvate in the presence of FrsA in which acetaldehyde and carbon dioxide were generated at the ratio of 1:1 (FIG. 1C). To exclude the possibility that the results are affected by the contaminant contained in FrsA, each cell extracts from frsA deleted mutants and wild-type *E. coli* was added to the solution containing pyruvate. As a result in the sample to which the wild-type extract was added, acetaldehyde was increased in a concentration dependent manner. In contrast in the sample to which the mutant extract was added, no acetaldehyde was detected (FIG. 3). This indicates that FrsA has a catabolic activity on pyruvates.

B. Substrate Specificity

Figure 4A:
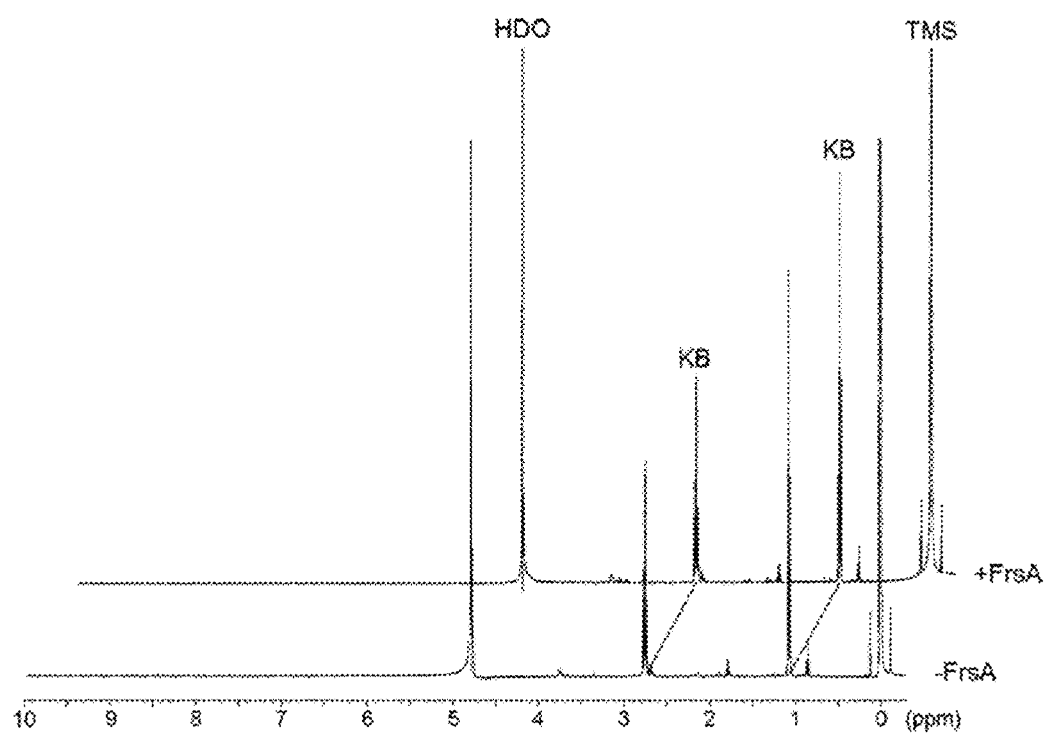
FIG. 4A is $^1$H-NMR spectra at 500 MHz of the reaction mixture of FrsA and α-ketobutyrate. Abbreviations: KB, α-ketobutyrate; TMS, tetramethylsilane.
Figure 4B:
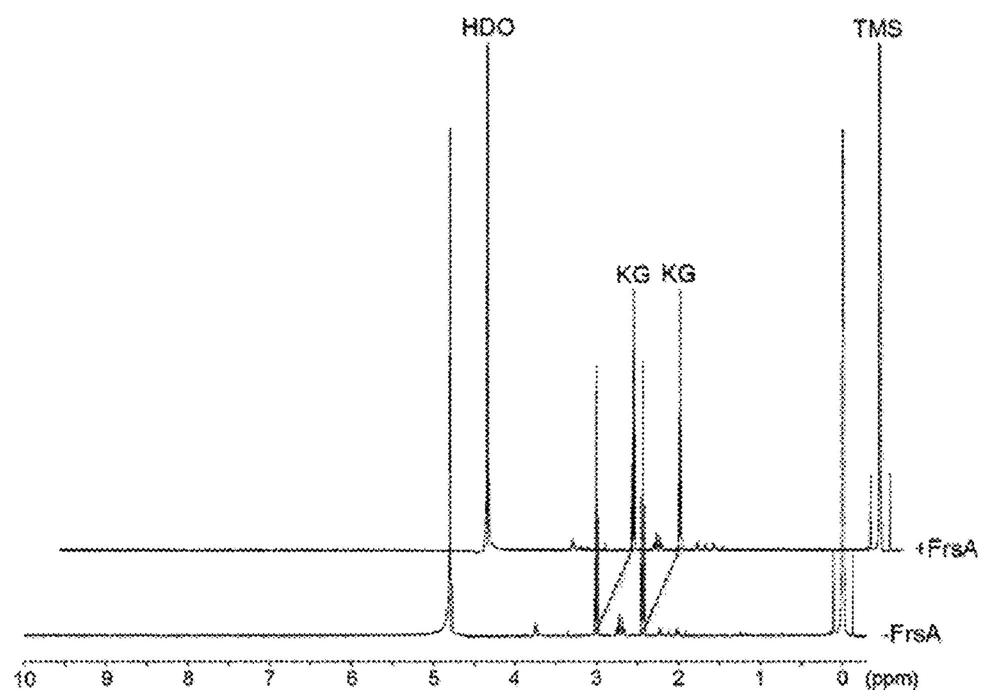
FIG. 4B is $^1$H-NMR spectra at 500 MHz of the reaction mixture of FrsA and α-ketobutyrate and α-ketoglutarate and pure acetaldehyde. Abbreviations: KG, α-ketoglutarate; TMS, tetramethylsilane.
Figure 4C:
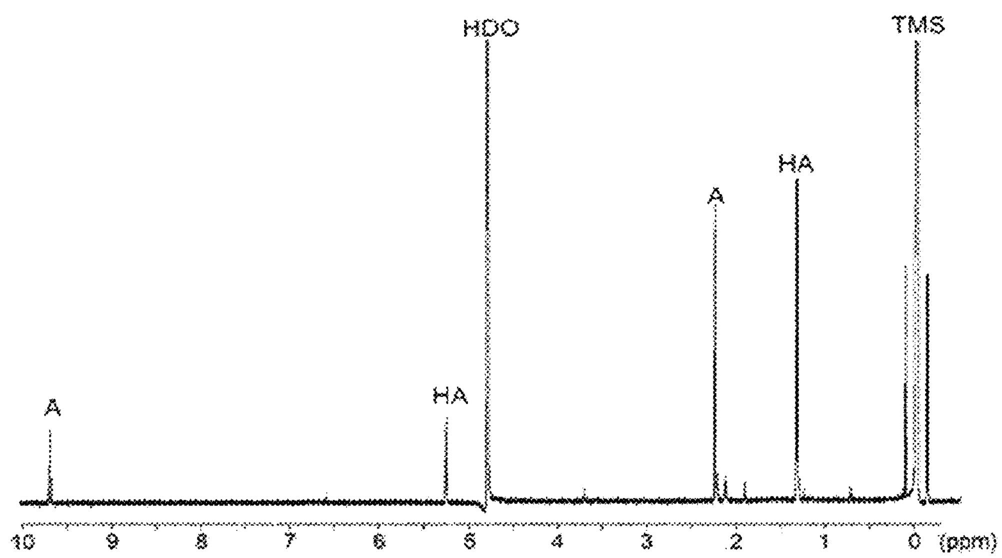
FIG. 4C is $^1$H-NMR spectra at 500 MHz of pure acetaldehyde. Abbreviations: A (acetaldehyde: at 2.24 and 9.68 ppm)' HA (hydrated acetaldehyde: at 1.33 and 5.25 ppm); HDO (deuterium oxide).
Figure 6:
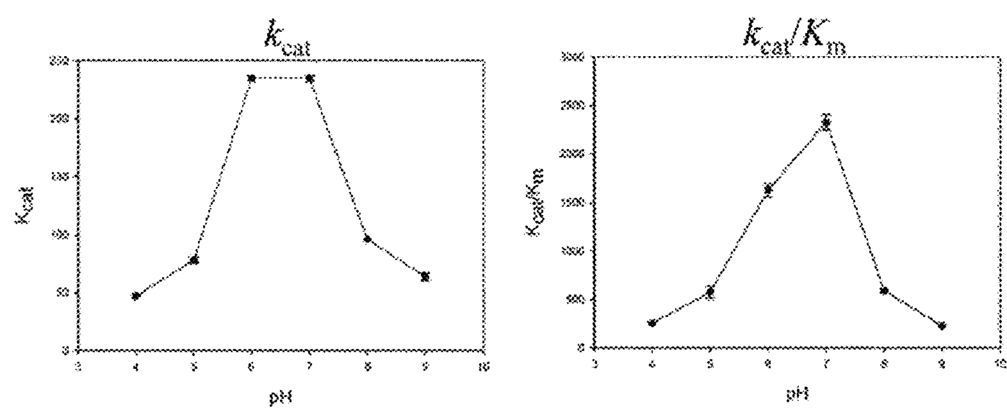
FIG. 6 are graphs showing pH dependency of the reaction catalyzed by FrsA. The recombinant FrsA was added to the reaction mixtures titrated to various pH ranging from 4 to 9, and then its enzyme kinetic parameters were determined using alcohol dehydrogeanse (ADH) assay kit as described in the Examples. The values of kcat and kcat/Km for the conversion of pyruvate to acetaldehyde were determined using standard curves of ADH reaction performed under the corresponding pH condition.

Further to prove the substrate specificity to pyruvate, various substrate such as acetate, lactate, oxaloacetate, α-ketoglutarate, and α-ketobutyrate were used in the same reaction as described above instead of pyruvate. Based on NMR data, it was found that no carbon dioxide was generated in the substrates other than pyruvate (FIGS. 4A, 4B and 4C).

C. Activity in Cells

Figure 1D:
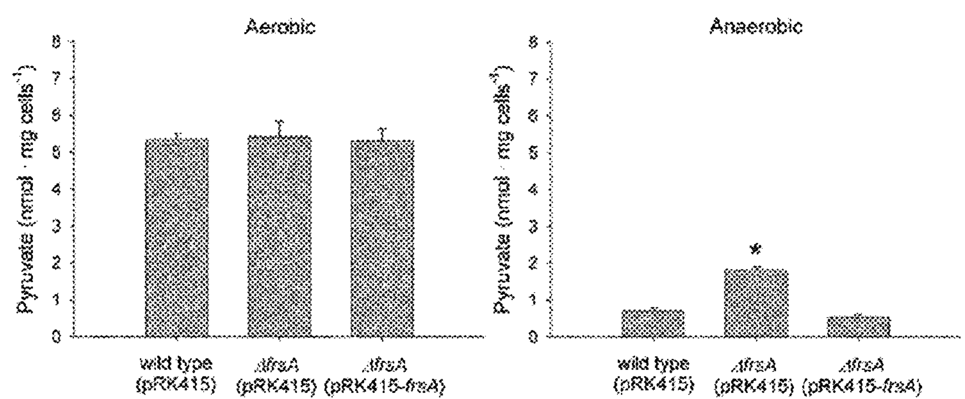
FIGS. 1D and 1E are graphs each showing cellular levels of pyruvate and acetaldehyde in bacteria expressing wild-type or mutant FrsA, respectively, which were grown in LBS-glucose medium under anaerobic (closed bars) or aerobic (open bars) condition. The bacteria comprise a FrsA gene in a wide-host-range vector pRK415. The data represents an average of three independent experiments and SD stands for standard deviation. Asterisks indicate p-value <0.0001 (Student t-test).
Figure 1E:
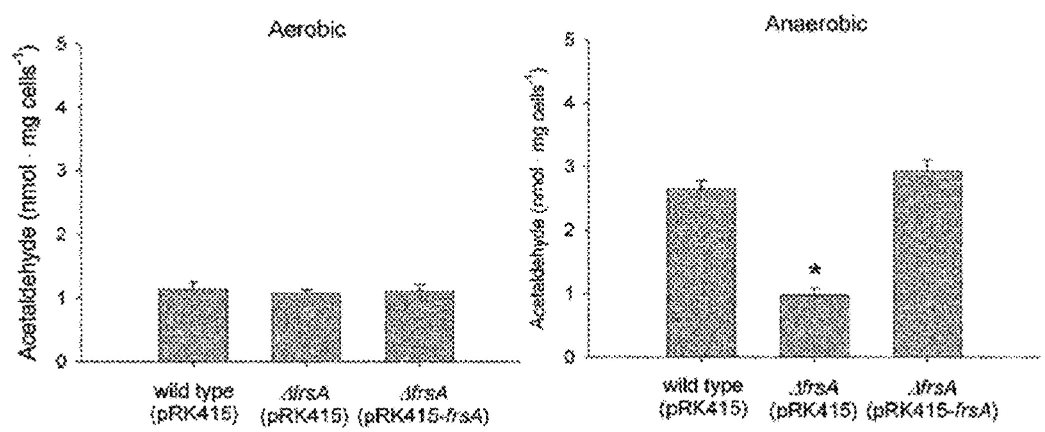

Then to confirm the activity of FrsA in cells, the concentrations of pyruvate in *V. vulnificus* and in frsA deleted mutant of Example 1 which were incubated in the presence of glucose were compared. As a result, the pyruvate concentration was found to be 3 times higher in the frsA deleted mutant than those of *V. vulnificus* under anaerobic condition. In contrast, the concentration was found to be similar under aerobic condition (FIG. 1D). This indicates that the deletion of frsA gene has resulted in a problem of utilizing pyruvate during the fermented metabolism process, which is in consistent with the result of aldehyde concentration monitoring. That is, the concentration of acetaldehyde in frsA mutant under anaerobic condition is 3 times lower than that found in wild-type (FIG. 1E). However, when a vector having a wide host range and carrying frsA gene was transformed into a frsA deleted mutant, the concentrations of pyruvate and acetaldehyde were recovered to a normal level (FIGS. 1D and 1E). Under aerobic condition, no difference was found between the wild-type and the mutant, which is due to the decrease in the FrsA expression under aerobic condition.

These results indicate that FrsA catalyzes the pyruvate decarboxylation reaction to decompose the pyruvate into acetaldehyde and carbon dioxide. According to the reaction rate analyses, FrsA is an efficient enzyme having a high catalytic activity having $k_{cat}$ and $k_{cat}$/km of 1,372 11 $s^{-1}$ and 3,518 183 $s^{-1}mM^{-1}$, respectively, which is 8 times higher value compared to PDC (pyruvate dehydrogenase complex), and becomes 17 times higher when $IIA^{Glc}$ was added. (Table 1). Thus FrsA enzyme has an activity enough to catalyze the fermentation in cells.

TABLE 1

Summary of the kinetic parameters obtained for FrsA[a] and PDC

| | $K_m$ (mM) | $k_{cat}$ ($sec^{-1}$) | $k_{cat}/K_m$ ($sec^{-1}$ $mM^{-1}$) |
|---|---|---|---|
| FrsA | | | |
| Wildtype | 0.39 ± 0.02 | 1,372 ± 11 | 3,518 ± 183 |
| Wildtype | | | |
| +dephospho-$IIA^{Glc}$ | 0.39 ± 0.03 | 2,980 ± 158 | 7,641 ± 713 |
| +phospho-$IIA^{Glc}$ | 0.39 ± 0.01 | 1,311 ± 48 | 3,362 ± 150 |
| PDC | | | |
| *Zymomonas mobilis*[22] | 0.40 | 180 | 450 |
| *Saccharomyces cerevisiae*[23] | 2.29 | 73 | 32 |

[a]Averages and standard deviations (in parentheses) were derived from at least three independent assays.

Example 3

Construction of Frsa Expression Plasmid and Production of Ethanol Using the Same 3-1 Construction of expression plasmid pXMJ-pdc/adhB cloning Genomic DNA from *Zymomonas mobilis* ZM4 (ATCC31821) as a template and primers [ZmPDC FPstI (5'-GATCCTGCAGAAAGGAGGACAACCATGAGT TATA CTGTCGGTAC-3'(SEQ ID NO: 21); PstI restriction site is underlined) and ZmPDC RXbaI (5'-GATC TCTAGACTAGAGGAGCTTGTTAACAG-3'(SEQ ID NO: 22); XbaI restriction site is underlined)] as primers were used for PCR to amplify full length pdc gene of 1,721-bp in size. Then the amplified fragment was digested with PstI and XbaI and cloned into an expression vector pXMJ19 (M. Jakoby et al. 1999. Construction and application of new *Corynebacterium glutamicum* vectors. Biotechnology Techniques. 13:437441)) to obtain pXMJ-pdc. Then to clone pXMJ-pdc/adhB, genomic DNA from *Zymomonas mobilis* ZM4 as a template and primers [ZmadhB FK (5'-GG GGTACCAAAGGAGGACAACCTAGCTATGGCTTCTT CAACTTTTTATATTC C-3'(SEQ ID NO: 23); KpnI restriction site is underlined) and ZmadhB RE (5'-CG GAATTCTTAGAAAGCGCTCAGGAAGAGTTC-3'(SEQ ID NO: 24); EcoRI restriction site is underlined)] as primers were used for PCR to amplify full length adhB gene of 1,171-bp in size. Then the fragment was digested with KpnI and EcoRI and cloned into pXMJ-pdc plasmid to obtain pXMJ-pdc/adhB.

pXMJ-frsA/crr/adhB cloning

Genomic DNA from *V. vulnificus* (Wright, A. C., Simpson, L. M., Oliver, J. D. & Morris, J. G., Jr. Phenotypic evaluation of acapsular transposon mutants of *Vibrio vulnificus*. *Infect Immun* 58, 1769-73 (1990)) as a template and [VvfrsAFP(5'-AA CTGCAGAAAGGAGGACAACCCCGAATATGTCAGA AGAAGTCAGC-3'(SEQ ID NO: 25); PstI restriction site is underlined) and VvfrsA RX (5'-GC TCTAGAGATTTGTCACCTTAAGAGTTCATC-3'(SEQ ID NO: 26); XbaI restriction site is underlined)] as primers were used for PCR to amplify full length frsA gene of 1,264-bp in size. The amplified DNA was then digested with PstI and XbaI and cloned into an expression vector pXMJ19 to obtain pXMJ-frsA. Then to clone pXMJ-frsA/crr, genomic DNA from *V. vulnificus* as a template and [VvcrrFBamHI(5'-CTAGGGATCCAAAGGAGGACAACCGA CAC AATGGGTCTGTTTGACAAAC-3'(SEQ ID NO: 27); BamHI restriction site is underlined) and VvcrrRKpnI(5'-GGGGTACCGTAGTAATTACTTAGTTACG CGTAG-3' (SEQ ID NO: 28); KpnI restriction site is underlined)] as primers were used for PCR to amplify a full length crr gene of 524-bp in size. The amplified DNA was then digested with BamHI and KpnI and cloned into a pXMJ-frsA plasmid to obtain pXMJ-frsA/crr. Genomic DNA from *V. vulnificus* ZM4 as a template and [ZmadhB FK (5'-GG GGTACCAAAGGAGGACAACCTAGCTATGGCTTCTT CAACTTTTTATATTC C-3'(SEQ ID NO: 29); KpnI restriction site is underlined) and ZmadhB RE (5'-CG GAATTCTTAGAAAGCGCTCAGGAAGAGTTC-3'(SEQ ID NO: 30); EcoRI restriction site is underlined)] as primers were used for PCR to amplify a full length adhB gene of 1,171-bp in length. The amplified product was then digested with KpnI and EcoRI and cloned into a pXMJ-frsA/crr plasmid to obtain pXMJ-frsA/crr/adhB.

pXMJ-frsA[mt]/crr/adhB Cloning pQE-frsAC131A plasmid encoding FrsA having a substitution at residue 131 from cysteine to alanine as prepared in Example 1-3 was used as a template and two primers [VvfrsA[mt] FP(5'-AACTGCAGAAAGGAGGACAA CCTA GCTATGGCCATAGAAACCTCGGCATTG-3'(SEQ ID NO: 31); PstI restriction site is underlined) and VvfrsA RX (5'-GCTCTAGAGATTTGTCACCTTAAGA GTTCATC-3'(SEQ ID NO: 32); XbaI restriction site is underlined)] were used for PCR to amplify frsA DNA fragment of 1,210-bp in length. Then the amplified product was digested with PstI and XbaI and cloned into an expression vector pXMJ19 to obtain pXMJ-frsA[mt]. Then to clone pXMJ-frsA[mt]/crr, genomic DNA from *V. vulnificus* as a template and two primers [VvcrrFBamHI (5'-CTAG GGATCCAAAGGAGGACAACCGACACAATGGGTCT GTTTGACAAAC-3'(SEQ ID NO: 33); BamHI restriction site is underlined) and VvcrrRKpnI (5'-GG GGTACCGTAGTAATTACTTAGTTACGCGTAG-3'(SEQ ID NO: 34); KpnI restriction site is underlined)] were used for PCR to amplify a full length crr gene of 524-bp in length. Then the amplified product was then digested with BamHI and KpnI and cloned into pXMJ-frsA[mt] to obtain pXMJ-frsA[mt]/crr. Then genomic DNA from *Zymomonas mobilis* ZM4 was used as a template and [ZmadhB FK (5'-GG GGTACCAAAGGAGGACAACCTAGCTATGGCTTCTT CAACTTTTTATATTC C-3'(SEQ ID NO: 35); KpnI restriction site is underlined) and ZmadhB RE (5'-CG GAATTCTTAGAAAGCGCTCAGGAAGAGTTC-3'(SEQ ID NO: 36); EcoRI restriction site is underlined)] as primers were used for PCR to amplify a full length adhB gene of 1,171-bp DNA in length. The amplified product was then digested with KpnI and EcoRI and cloned into pXMJ-frsA [mt]/crr to obtain pXMJ-frsA[mt]/crr/adhB.

3-2 Production of Ethanol Using *E. coli*

Overexpression of FrsA/IIA$^{Glc}$ in *E. coli*

Each of the plasmids constructed in Example 3-1 was introduced into *E. coli* K12 (*Escherichia coli* K-12 F-prime factors, old and new. Bacteriological Reviews. 36:587-607) and the transformed cells were grown in a medium used for ethanol production (LB, 5% glucose) at 37° C. without shaking. *E. coli* K12 was treated with 100 mM MES buffer (2-(N-morpholino)ethanesulfonic acid) at 0 and 12 hours during the culture to prevent an abrupt drop of pH by adding 100 mM MES to the LB medium containing 100 mM MES and 5% glucose, which increased pH of the medium. All the media for culturing contained 4 μg/ml of chloramphenicol.

In the meantime, ADH analyses were performed to measure the amount of ethanol produced on aliquots of sample taken at the indicated time during the incubation. Specifically 990 μl of reaction buffer (glycine 500 mM, hydrazine sulfate 75 mM, sodium pyrophosphate tetrabasic 75 mM, 3.7 unit ADH, 5 mM NAD$^+$, pH 9.0) was mixed with 10 μl of sample, and the mixture was then incubated at 37° C. for 30 min. After the incubation, NADH produced was measured by taking absorptions at 340 nm. Then the values were used to determine the concentration of ethanol produced by the extrapolation from the calibration curve for ethanol. Results are shown in FIG. 7A.

As a result, it was found that there is no difference in the amount of ethanol produced when FrsA (pXMJ-frsA/adh) was overexpressed in *E. coli*. However when FrsA and IIA$^{Glc}$ (pXMJ-frsA/crr/adh) were overexpressed, the amount of ethanol produced was increased about 310% compared to the control. The amount of ethanol produced when FrsA/IIA$^{Glc}$ (pXMJ-frsA/crr/adh) was overexpressed was found to be 42% of the amount produced when Pyruvate Decarboxyalse (PDC) (pXMJ-pdc/adh) was overexpressed.

Improvement of Ethanol Production by Controlling pH of the Media

Figure 7A:
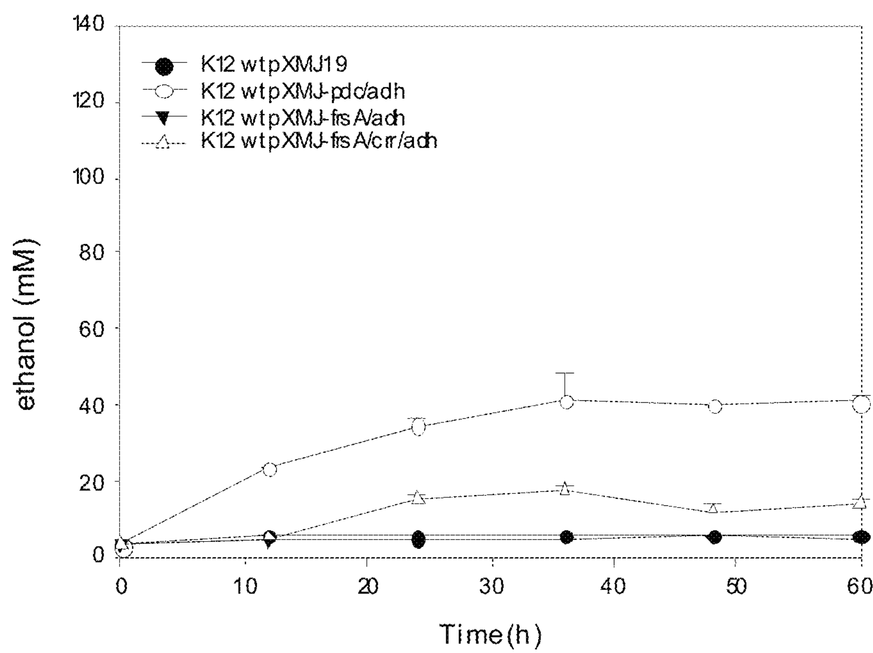
FIG. 7A is a graph showing the amount of ethanol produced with time by *E. coli* K12 strains transformed with various plasmids constructed in the present disclosure (wild-type *E. coli* K12 carrying pXMJ19 [closed circle], pXMJ-pdc/adh [open circle], pXMJ-frsA/adh closed inverted triangle], pXMJ-frsA/crr/adh [open triangle]). *E. coli* strains were batch cultured in 5% glucose containing LB at 30° C. with mild shaking. The cultured medium was analyzed by enzyme based ethanol.
Figure 7B:
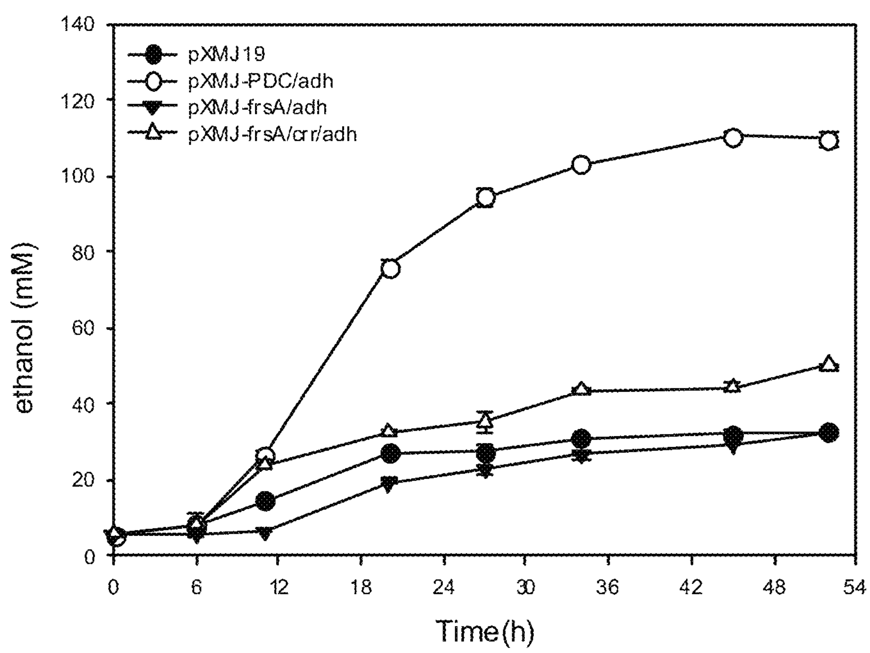
FIG. 7B is a graph showing that the amount of ethanol produced by *E. coli* K12 strains transformed with various plasmids constructed in the present disclosure (wild-type *E. coli* K12 carrying pXMJ19 [closed circle], pXMJ-pdc/adh [open circle], pXMJ-frsA/adh closed inverted triangle], pXMJ-frsA/crr/adh [open triangle]) has increased by controlling pH of the medium by adding MES buffer thereto.

The ethanol productivity by overexpression of FrsA/IIA$^{Glc}$ (pXMJ-frsA/crr/adh) was found to be increased about 254% when pH of the media was controlled by addition of MES buffer compared to the control in which pH was not controlled (FIG. 7A). Also the amount produced was increased about 138% compared to the control when pH was controlled and was about 42% compared to the amount when PDC(pXMJ-pdc/adh) was overexpressed (FIGS. 7A and B).

These results indicate that the present FrsA is a novel PDC enzyme which can be used to produce ethanol by replacing PDC. Also the ethanol production can be increased by controlling pH of the medium employed.

3-3 Production of Ethanol Using *Corynebacterium glutamicum*

Production of Ethanol Using Corvnebacterium *Glutamicum* Overexpressing FrsA/IIA$^{Glc}$ Each of the plasmids constructed in Example 3-1 was introduced into *Corynebacterium glutamicum* ATCC 13032. And the transformed cells were grown in a medium used for ethanol production (LB, 5% glucose) at 30° C. with shaking. All the media used for culturing contained 10 μg/ml of chloramphenicol.

Figure 8A:
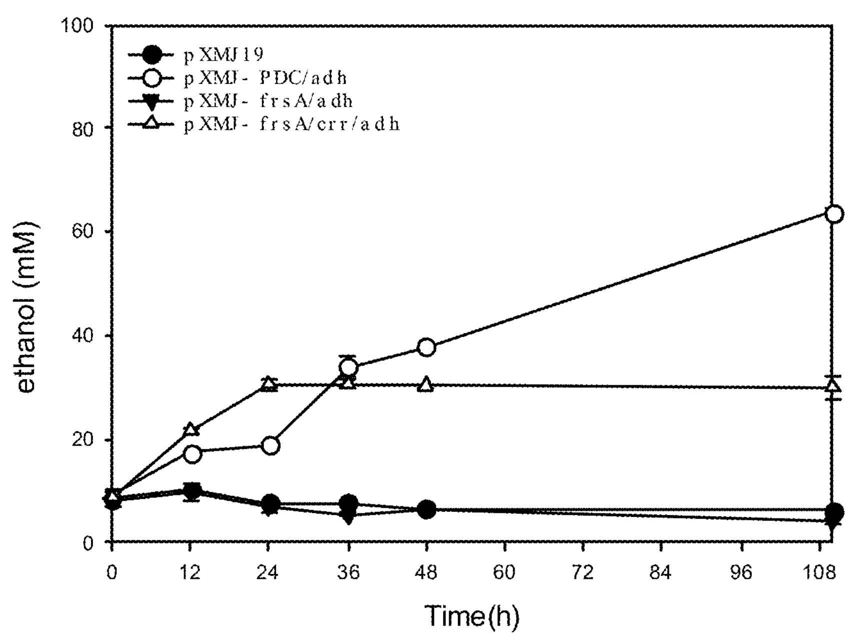
FIG. 8A is a graph showing the amount of ethanol produced with time by *C. glutamicum* transformed with various plasmids constructed in the present disclosure (wild-type *C. glutamicum* ATCC 13032 carrying pXMJ19 [closed circle], pXMJ-pdc/adh [open circle], pXMJ-frsA/adh closed inverted triangle], pXMJ-frsA/crr/adh [open triangle]).

In the meantime, ADH analyses were performed as described in 3-2 to measure the amount of ethanol produced on aliquots of supernatant of the sample taken at the indicated time during the incubation. Results are shown in FIG. 8A.

As a result, it was found that there is no difference in the amount of ethanol produced when FrsA (pXMJ-frsA/adh) was overexpressed in *C. glutamicum*. However when FrsA/

IIAGlc(pXMJ-frsA/crr/adh) was overexpressed, the ethanol production was increased about 2341% compared to the control.

Ethanol Production Using FrsA[mt] Mutant

Figure 8C:
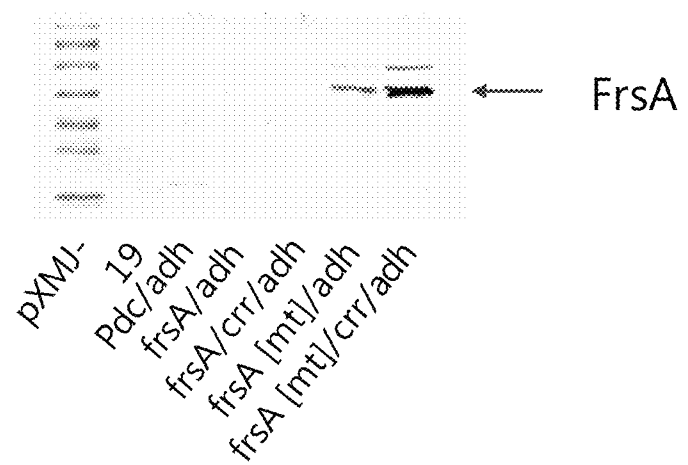
FIG. 8C is a result of western blot analysis using culture of *C. glutamicum* carrying pXMJ-19, pXMJ-pdc/adh, pXMJ-frsA/adh, pXMJ-frsA/crr/adh, pXMJ-FrsA[mt]/adh and pXMJ-FrsA[mt]/crr/adh.

The mutant FrsA was generated as described in Example 3-1 to improve its stability in host cells. As shown in FIG. 8B, mutant FrsA[mt] has a deletion from residues 2 to 19 from the N-terminal region and a substitution at residue 131 from cysteine to alanine. Results are shown in FIG. 8C which indicates that the stability of FrsA[mt] was increased in *C. glutamicum* evident from the amount of wild type and mutant FrsA after their overexpression in the cells and SDS-PAGE analysis.

Various plasmids carrying FrsA[mt] (pXMJ-pdc/adh, pXMJ-frsA[mt]/adh, pXMJ-frsA[mt]/crr/adh) were constructed and introduced into *C. glutamicum* and the amount of ethanol produced was determined with time as described in Example 3-2.

Figure 8D:
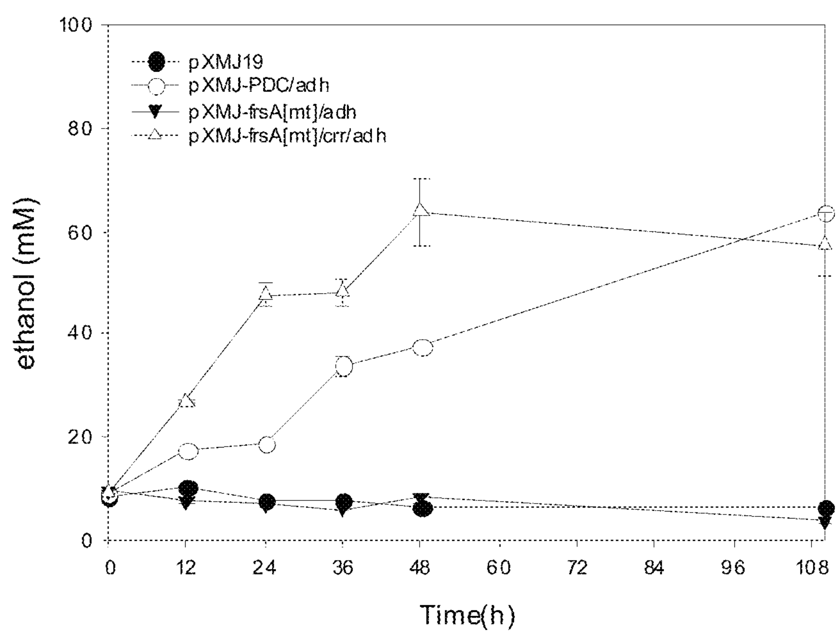
FIG. 8D is a graph showing the amount of ethanol produced with time in cultures of *C. glutamicum* (wild-type *C. glutamicum* ATCC 13032 carrying pXMJ19 [closed circle], pXMJ-pdc/adh [open circle], pXMJ-FrsA[mt]/ADH closed inverted triangle], pXMJ-FrsA[mt]/IIA$^{Glc}$/ADH [open triangle]).

Results are shown in FIG. 8D. As a result, it was found that there is no difference in the amount of ethanol produced when FrsA (pXMJ-frsA/adh) was overexpressed in *C. glutamicum*. However when FrsA/IIAGlc(pXMJ-frsA/crr/adh) was overexpressed, the ethanol production was increased about 2341% compared to the control.

These results indicate that *C. glutamicum* can be advantageously used for the ethanol production as a host. Also FrsA[mt] mutant proteins can be advantageously used for ethanol production due to its stability in cells.

The various singular/plural permutations may be expressly set forth herein for sake of clarity. Although a few embodiments of the present disclosure have been shown and described, it would be appreciated by those skilled in the art that changes may be made in this embodiment without departing from the principles and sprit of the invention, the scope of which is defined in the claims and their equivalents.

REFERENCES

1. LIN, Y. & S. TANAKA. Ethanol fermentation from biomass resources: current state and prospects. Appl. Microbiol. Biotechnol. 69: 62742 (2006).
2. DIEN, B. S., M. A. COTTA & T. W. JEFFRIES. Bacteria engineered for fuel ethanol production: current status. Appl. Microbiol. Biotechnol. 63: 25866 (2003).
3. Wright, A. C., Simpson, L. M., Oliver, J. D. & Morris, J. G., Jr. Phenotypic evaluation of acapsular transposon mutants of *Vibrio vulnificus*. *Infect Immun* 58, 1769-73 (1990).
4. Sambrook, J. & Russell, D. W. *Molecular cloning: a laboratory manual*, (Cold Spring Harbor Laboratory Press, Cold Spring Harbor, N.Y., 2001).
5. Anand, Rishi D. et al. Restriction digestion monitors facilitate plasmid construction and PCR cloning. *BioTechniques* 36:982-985 (2004).
6. Simon, R., Priefer, U. & Puhler, A. A Broad Host Range Mobilization System for *In Vivo Genetic Engineering: Transposon Mutagenesis in Gram Negative Bacteria. Nat Biotechnol* 1, 784-791 (1983).
7. Park, K. J. et al. Isolation and characterization of rpoS from a pathogenic bacterium, *Vibrio vulnificus*: role of $\sigma^S$ in survival of exponential-phase cells under oxidative stress. *J Bacteriol* 186, 3304-12 (2004).
8. Ullrich, J. Yeast pyruvate decarboxylase (2-oxoacid acrboxylase, EC 4.1.1.1) assay of thiamine pyrophosphate. *Methods Enzymol.* 18, 109-115 (1970).
9. Koo, B. M. et al. A novel fermentation/respiration switch protein regulated by enzyme $IIA^{Glc}$ in *Escherichia coli. J Biol Chem* 279, 31613-21 (2004).
10. Gu, W., Bousfield, D. W. & Tripp, C. P. Formation of calcium carbonate particles by direct contact of Ca(OH)2 powders with supercritical CO2. *J Mater Chem* 16, 3312-3317 (2006).
11. Hinman, L. M. & Blass, J. P. An NADH-linked spectrophotometric assay for pyruvate dehydrogenase complex in crude tissue homogenates. *J Biol Chem* 256, 6583-6 (1981).
12. Stephenson, M. P. & Dawes, E. A. Pyruvic acid and formic acid metabolism in *Sarcina ventriculi and the role of ferredoxin. J Gen Microbiol* 69, 331-43 (1971).
13. Erecinska, M. & Silver, I. A. Tissue oxygen tension and brain sensitivity to hypoxia. *Respir Physiol* 128, 263-76 (2001).

What is claimed is:

1. An isolated polynucleotide encoding a mutant fermentation respiration switch (FrsA) protein, wherein the mutant FrsA protein has pyruvate decarboxylase activity, and wherein the mutant FrsA protein comprises the amino acid sequence of SEQ ID NO: 2, except that: (1) cysteine at the position corresponding to residue 131 of SEQ ID NO: 2 is replaced with alanine in the mutant FrsA protein, or (2) amino acids corresponding to residues 2-19 of SEQ ID NO: 2 are deleted and cysteine at the position corresponding to residue 131 of SEQ ID NO: 2 is replaced with alanine in the mutant FrsA protein.

2. The polynucleotide of claim 1, wherein the polynucleotide consists of the nucleotide sequence of SEQ ID NO: 5 or 7.

3. A vector comprising the polynucleotide according to claim 1.

4. A microorganism comprising the vector according to claim 3.

* * * * *

SEQUENCE LISTING

```
<160> NUMBER OF SEQ ID NOS: 42

<210> SEQ ID NO 1
<211> LENGTH: 1248
<212> TYPE: DNA
<213> ORGANISM: Vibrio vulnificus
<220> FEATURE:
<221> NAME/KEY: misc_feature
<222> LOCATION: (1)..(1248)
<223> OTHER INFORMATION: FrsA wild type gene

<400> SEQUENCE: 1

atgtcagaag aagtcagcaa aaacctgtca gaaacgctat ttgtcaaaca taagcaagcc      60

aaagaaacct cggcattgac tcaatacatg ccgaccagcc aatccttact tgatgaaatt     120

aaagagaaga atggtttttc ttggtatcgc aaccttcgtc gcttgcaatg ggtgtggcaa     180

ggtgtcgatc ctattgagca agaacaagta ttggctcgta ttgcctcttc caaacattca     240

cgcactgatg agcaatggct cgatacggtg atgggatatc acagtggtaa ctgggcttat     300

gaatggacga ggctcggtat ggagcatcaa aaacgtgccg gtgagatgac gaatgaagca     360

gcatcggaag cgctcttctc cgcatccttg tgttacagca tcgcaggtta cccacacctc     420
```

```
aagagcgata atttggccat tcaagcccag gtattggcca acagcgctta tcttgaagcc    480

gcgaaaaaaa gcaaatacat catcaagcag ctcgagatcc catttgagaa agggaagatc    540

accgcgcatt tgcatctgac caatacggac aaaccgcatc ctgtggttat tgtgagtgcg    600

ggattagaca gcttgcaaac agacatgtgg cgtctatttc gagatcacct tgccaagcac    660

gatattgcca tgttgacagt agacatgcca tcggtggggt acagctcaaa atacccatta    720

acggaggatt acagtcgcct tcaccaagcg gtgttgaacg agcttttctc tattccttat    780

gtcgatcatc atcgagtggg tttgatcggc tttcgttttg gcggtaacgc catggtgagg    840

ctctcgtttc ttgagcaaga aaagatcaaa gcgtgcgtca tcttaggcgc acctattcat    900

gatatttttg cctccccaca gaaattgcag caaatgccga agatgtatct cgatgtctta    960

gcctcgcgtt taggtaagag tgtggtagat atttacagct tatcggggca aatggccgcg   1020

tggtcactga aagtacaagg ctttttgagc agtcgtaaaa ccaaggtgcc tatcttggcg   1080

atgagcttag aaggggatcc ggtctcgcca tattcggata atcagatggt tgcttttttt   1140

agcacttatg gaaaagcgaa gaaaatcagt tccaaaacaa ttacacaagg atatgagcaa   1200

tccctcgatt tagcgataaa gtggctggaa gatgaactct taaggtga                1248
```

<210> SEQ ID NO 2
<211> LENGTH: 415
<212> TYPE: PRT
<213> ORGANISM: Vibrio vulnificus
<220> FEATURE:
<221> NAME/KEY: PEPTIDE
<222> LOCATION: (1)..(415)
<223> OTHER INFORMATION: FrsA wild type protein

<400> SEQUENCE: 2

```
Met Ser Glu Glu Val Ser Lys Asn Leu Ser Glu Thr Leu Phe Val Lys
1               5                   10                  15

His Lys Gln Ala Ile Glu Thr Ser Ala Leu Thr Gln Tyr Met Pro Thr
            20                  25                  30

Ser Gln Ser Leu Leu Asp Glu Ile Lys Glu Lys Asn Gly Phe Ser Trp
        35                  40                  45

Tyr Arg Asn Leu Arg Arg Leu Gln Trp Val Trp Gln Gly Val Asp Pro
    50                  55                  60

Ile Glu Gln Glu Gln Val Leu Ala Arg Ile Ala Ser Ser Lys His Ser
65                  70                  75                  80

Arg Thr Asp Glu Gln Trp Leu Asp Thr Val Met Gly Tyr His Ser Gly
                85                  90                  95

Asn Trp Ala Tyr Glu Trp Thr Arg Leu Gly Met Glu His Gln Lys Arg
            100                 105                 110

Ala Gly Glu Met Thr Asn Glu Ala Ala Ser Glu Ala Leu Phe Ser Ala
        115                 120                 125

Ser Leu Cys Tyr Ser Ile Ala Gly Tyr Pro His Leu Lys Ser Asp Asn
    130                 135                 140

Leu Ala Ile Gln Ala Gln Val Leu Ala Asn Ser Ala Tyr Leu Glu Ala
145                 150                 155                 160

Ala Lys Lys Ser Lys Tyr Ile Ile Lys Gln Leu Glu Ile Pro Phe Glu
                165                 170                 175

Lys Gly Lys Ile Thr Ala His Leu His Leu Thr Asn Thr Asp Lys Pro
            180                 185                 190

His Pro Val Val Ile Val Ser Ala Gly Leu Asp Ser Leu Gln Thr Asp
        195                 200                 205
```

```
Met Trp Arg Leu Phe Arg Asp His Leu Ala Lys His Asp Ile Ala Met
    210                 215                 220

Leu Thr Val Asp Met Pro Ser Val Gly Tyr Ser Ser Lys Tyr Pro Leu
225                 230                 235                 240

Thr Glu Asp Tyr Ser Arg Leu His Gln Ala Val Leu Asn Glu Leu Phe
                245                 250                 255

Ser Ile Pro Tyr Val Asp His His Arg Val Gly Leu Ile Gly Phe Arg
            260                 265                 270

Phe Gly Gly Asn Ala Met Val Arg Leu Ser Phe Leu Glu Gln Glu Arg
        275                 280                 285

Ile Lys Ala Cys Val Ile Leu Gly Ala Pro Ile His Asp Ile Phe Ala
    290                 295                 300

Ser Pro Gln Lys Leu Gln Gln Met Pro Lys Met Tyr Leu Asp Val Leu
305                 310                 315                 320

Ala Ser Arg Leu Gly Lys Ser Val Val Asp Ile Tyr Ser Leu Ser Gly
                325                 330                 335

Gln Met Ala Ala Trp Ser Leu Lys Val Gln Gly Phe Leu Ser Ser Arg
            340                 345                 350

Lys Thr Lys Val Pro Ile Leu Ala Met Ser Leu Glu Gly Asp Pro Val
        355                 360                 365

Ser Pro Tyr Ser Asp Asn Gln Met Val Ala Phe Phe Ser Thr Tyr Gly
    370                 375                 380

Lys Ala Lys Lys Ile Ser Ser Lys Thr Ile Thr Gln Gly Tyr Glu Gln
385                 390                 395                 400

Ser Leu Asp Leu Ala Ile Lys Trp Leu Glu Asp Glu Leu Leu Arg
                405                 410                 415
```

<210> SEQ ID NO 3
<211> LENGTH: 510
<212> TYPE: DNA
<213> ORGANISM: Vibrio vulnificus
<220> FEATURE:
<221> NAME/KEY: misc_feature
<222> LOCATION: (1)..(510)
<223> OTHER INFORMATION: IIAGlc gene

<400> SEQUENCE: 3

```
atgggtctgt ttgacaaact taagaagctt gtatctgatg acagcgctag cgccggtgca     60

atcgaaatta tcgcaccttt gtctggtgag atcgtgaaca tcgaagatgt gccagatgtt    120

gtttttgctg agaagatcgt tggtgacggt attgctatca aaccaacagg caacaaaatg    180

gtagctcctg taaacggtac tatcggtaag atctttgaaa ctaaccacgc attctctatc    240

gagtctgacg atggtgttga actgtttgtt cacttcggta tcgacacagt tgaactaaaa    300

ggcgaaggct tcactcgtat cgctgaagaa ggtcaaactg ttaaagctgg cgacactgta    360

attgaattcg atcttgctct tcttgaagag aaagcgaagt caacactaac tccagttgtt    420

atctctaaca tggacgaaat caaagagctg aataagcttt ctggttctgt tgttgttggt    480

gaaacaccag ttctacgcgt aactaagtaa                                     510
```

<210> SEQ ID NO 4
<211> LENGTH: 169
<212> TYPE: PRT
<213> ORGANISM: Vibrio vulnificus
<220> FEATURE:
<221> NAME/KEY: PEPTIDE
<222> LOCATION: (1)..(169)
<223> OTHER INFORMATION: IIAGlc protein

<400> SEQUENCE: 4

```
Met Gly Leu Phe Asp Lys Leu Lys Lys Leu Val Ser Asp Asp Ser Ala
  1               5                  10                  15

Ser Ala Gly Ala Ile Glu Ile Ile Ala Pro Leu Ser Gly Glu Ile Val
             20                  25                  30

Asn Ile Glu Asp Val Pro Asp Val Val Phe Ala Glu Lys Ile Val Gly
         35                  40                  45

Asp Gly Ile Ala Ile Lys Pro Thr Gly Asn Lys Met Val Ala Pro Val
     50                  55                  60

Asn Gly Thr Ile Gly Lys Ile Phe Glu Thr Asn His Ala Phe Ser Ile
 65                  70                  75                  80

Glu Ser Asp Asp Gly Val Glu Leu Phe Val His Phe Gly Ile Asp Thr
                 85                  90                  95

Val Glu Leu Lys Gly Glu Gly Phe Thr Arg Ile Ala Glu Glu Gly Gln
            100                 105                 110

Thr Val Lys Ala Gly Asp Thr Val Ile Glu Phe Asp Leu Ala Leu Leu
        115                 120                 125

Glu Glu Lys Ala Lys Ser Thr Leu Thr Pro Val Val Ile Ser Asn Met
    130                 135                 140

Asp Glu Ile Lys Glu Leu Asn Lys Leu Ser Gly Ser Val Val Val Gly
145                 150                 155                 160

Glu Thr Pro Val Leu Arg Val Thr Lys
                165
```

<210> SEQ ID NO 5
<211> LENGTH: 1248
<212> TYPE: DNA
<213> ORGANISM: Artificial Sequence
<220> FEATURE:
<223> OTHER INFORMATION: gene encoding FrsA with substitution at 131 from Cystein to Alanine
<220> FEATURE:
<221> NAME/KEY: misc_feature
<222> LOCATION: (391)..(393)
<223> OTHER INFORMATION: Cys to Ala substitution

<400> SEQUENCE: 5

```
atgtcagaag aagtcagcaa aaacctgtca gaaacgctat ttgtcaaaca taagcaagcc     60

aaagaaacct cggcattgac tcaatacatg ccgaccagcc aatccttact tgatgaaatt    120

aaagagaaga atggtttttc ttggtatcgc aaccttcgtc gcttgcaatg ggtgtggcaa    180

ggtgtcgatc ctattgagca agaacaagta ttggctcgta ttgcctcttc caaacattca    240

cgcactgatg agcaatggct cgatacggtg atgggatatc acagtggtaa ctgggcttat    300

gaatggacga ggctcggtat ggagcatcaa aaacgtgccg gtgagatgac gaatgaagca    360

gcatcggaag cgctcttctc cgcatccttg gcgtacagca tcgcaggtta cccacacctc    420

aagagcgata atttggccat tcaagcccag gtattggcca acagcgctta tcttgaagcc    480

gcgaaaaaaa gcaaatacat catcaagcag ctcgagatcc catttgagaa agggaagatc    540

accgcgcatt tgcatctgac caatacggac aaaccgcatc ctgtggttat tgtgagtgcg    600

ggattagaca gcttgcaaac agacatgtgg cgtctatttc gagatcacct tgccaagcac    660

gatattgcca tgttgacagt agacatgcca tcggtggggt acagctcaaa atacccatta    720

acggaggatt acagtcgcct tcaccaagcg gtgttgaacg agcttttctc tattccttat    780

gtcgatcatc atcgagtggg tttgatcggc tttcgttttg gcggtaacgc catggtgagg    840
```

```
ctctcgtttc ttgagcaaga aaagatcaaa gcgtgcgtca tcttaggcgc acctattcat    900

gatatttttg cctccccaca gaaattgcag caaatgccga agatgtatct cgatgtctta    960

gcctcgcgtt taggtaagag tgtggtagat atttacagct tatcggggca aatggccgcg   1020

tggtcactga aagtacaagg ctttttgagc agtcgtaaaa ccaaggtgcc tatcttggcg   1080

atgagcttag aaggggatcc ggtctcgcca tattcggata atcagatggt tgcttttttt   1140

agcacttatg gaaaagcgaa gaaaatcagt tccaaaacaa ttacacaagg atatgagcaa   1200

tccctcgatt tagcgataaa gtggctggaa gatgaactct taaggtga                1248


<210> SEQ ID NO 6
<211> LENGTH: 415
<212> TYPE: PRT
<213> ORGANISM: Artificial Sequence
<220> FEATURE:
<223> OTHER INFORMATION: FrsA with substitution at 131 from Cystein to
      Alanine
<220> FEATURE:
<221> NAME/KEY: VARIANT
<222> LOCATION: (131)
<223> OTHER INFORMATION: Cys to Ala substitution

<400> SEQUENCE: 6

Met Ser Glu Glu Val Ser Lys Asn Leu Ser Glu Thr Leu Phe Val Lys
  1               5                  10                  15

His Lys Gln Ala Ile Glu Thr Ser Ala Leu Thr Gln Tyr Met Pro Thr
             20                  25                  30

Ser Gln Ser Leu Leu Asp Glu Ile Lys Glu Lys Asn Gly Phe Ser Trp
         35                  40                  45

Tyr Arg Asn Leu Arg Arg Leu Gln Trp Val Trp Gln Gly Val Asp Pro
     50                  55                  60

Ile Glu Gln Glu Gln Val Leu Ala Arg Ile Ala Ser Ser Lys His Ser
 65                  70                  75                  80

Arg Thr Asp Glu Gln Trp Leu Asp Thr Val Met Gly Tyr His Ser Gly
                 85                  90                  95

Asn Trp Ala Tyr Glu Trp Thr Arg Leu Gly Met Glu His Gln Lys Arg
            100                 105                 110

Ala Gly Glu Met Thr Asn Glu Ala Ala Ser Glu Ala Leu Phe Ser Ala
        115                 120                 125

Ser Leu Ala Tyr Ser Ile Ala Gly Tyr Pro His Leu Lys Ser Asp Asn
    130                 135                 140

Leu Ala Ile Gln Ala Gln Val Leu Ala Asn Ser Ala Tyr Leu Glu Ala
145                 150                 155                 160

Ala Lys Lys Ser Lys Tyr Ile Ile Lys Gln Leu Glu Ile Pro Phe Glu
                165                 170                 175

Lys Gly Lys Ile Thr Ala His Leu His Leu Thr Asn Thr Asp Lys Pro
            180                 185                 190

His Pro Val Val Ile Val Ser Ala Gly Leu Asp Ser Leu Gln Thr Asp
        195                 200                 205

Met Trp Arg Leu Phe Arg Asp His Leu Ala Lys His Asp Ile Ala Met
    210                 215                 220

Leu Thr Val Asp Met Pro Ser Val Gly Tyr Ser Ser Lys Tyr Pro Leu
225                 230                 235                 240

Thr Glu Asp Tyr Ser Arg Leu His Gln Ala Val Leu Asn Glu Leu Phe
                245                 250                 255

Ser Ile Pro Tyr Val Asp His His Arg Val Gly Leu Ile Gly Phe Arg
            260                 265                 270
```

```
Phe Gly Gly Asn Ala Met Val Arg Leu Ser Phe Leu Glu Gln Glu Arg
        275                 280                 285

Ile Lys Ala Cys Val Ile Leu Gly Ala Pro Ile His Asp Ile Phe Ala
    290                 295                 300

Ser Pro Gln Lys Leu Gln Gln Met Pro Lys Met Tyr Leu Asp Val Leu
305                 310                 315                 320

Ala Ser Arg Leu Gly Lys Ser Val Val Asp Ile Tyr Ser Leu Ser Gly
                325                 330                 335

Gln Met Ala Ala Trp Ser Leu Lys Val Gln Gly Phe Leu Ser Ser Arg
            340                 345                 350

Lys Thr Lys Val Pro Ile Leu Ala Met Ser Leu Glu Gly Asp Pro Val
        355                 360                 365

Ser Pro Tyr Ser Asp Asn Gln Met Val Ala Phe Phe Ser Thr Tyr Gly
    370                 375                 380

Lys Ala Lys Lys Ile Ser Ser Lys Thr Ile Thr Gln Gly Tyr Glu Gln
385                 390                 395                 400

Ser Leu Asp Leu Ala Ile Lys Trp Leu Glu Asp Glu Leu Leu Arg
                405                 410                 415


<210> SEQ ID NO 7
<211> LENGTH: 1194
<212> TYPE: DNA
<213> ORGANISM: Artificial Sequence
<220> FEATURE:
<223> OTHER INFORMATION: frsA mutant gene with deletion from 2-19 aa and
      substitution at 131 aa (Cystein to Alanine) compred to wild type
      gene

<400> SEQUENCE: 7

atggccatag aaacctcggc attgactcaa tacatgccga ccagccaatc cttacttgat     60

gaaattaaag agaagaatgg tttttcttgg tatcgcaacc ttcgtcgctt gcaatgggtg    120

tggcaaggtg tcgatcctat tgagcaagaa caagtattgg ctcgtattgc ctcttccaaa    180

cattcacgca ctgatgagca atggctcgat acggtgatgg gatatcacag tggtaactgg    240

gcttatgaat ggacgaggct cggtatggag catcaaaaac gtgccggtga gatgacgaat    300

gaagcagcat cggaagcgct cttctccgca tccttggctt acagcatcgc aggttaccca    360

cacctcaaga gcgataattt ggccattcaa gcccaggtat tggccaacag cgcttatctt    420

gaagccgcga aaaaaagcaa atacatcatc aagcagctcg agatcccatt tgagaaaggg    480

aagatcaccg cgcatttgca tctgaccaat acggacaaac cgcatcctgt ggttattgtg    540

agtgcgggat tagacagctt gcaaacagac atgtggcgtc tatttcgaga tcaccttgcc    600

aagcacgata ttgccatgtt gacagtagac atgccatcgg tggggtacag ctcaaaatac    660

ccattaacgg aggattacag tcgccttcac caagcggtgt tgaacgagct tttctctatt    720

ccttatgtcg atcatcatcg agtgggtttg atcggctttc gttttggcgg taacgccatg    780

gtgaggctct cgtttcttga gcaagaaagg atcaaagcgt gcgtcatctt aggcgcacct    840

attcatgata tttttgcctc cccacagaaa ttgcagcaaa tgccgaagat gtatctcgat    900

gtcttagcct cgcgtttagg taagagtgtg gtagatattt acagcttatc ggggcaaatg    960

gccgcgtggt cactgaaagt acaaggcttt ttgagcagtc gtaaaaccaa ggtgcctatc   1020

ttggcgatga gcttagaagg ggatccggtc tcgccatatt cggataatca gatggttgct   1080

ttttttagca cttatggaaa agcgaagaaa atcagttcca aaacaattac acaaggatat   1140

gagcaatccc tcgatttagc gataaagtgg ctggaagatg aactcttaag gtga         1194
```

```
<210> SEQ ID NO 8
<211> LENGTH: 397
<212> TYPE: PRT
<213> ORGANISM: Artificial Sequence
<220> FEATURE:
<223> OTHER INFORMATION: FrsA with substitution at 131 from Cystein to
      Alanine and deletion from 2-18 compared to wild type

<400> SEQUENCE: 8

Met Ala Ile Glu Thr Ser Ala Leu Thr Gln Tyr Met Pro Thr Ser Gln
  1               5                  10                  15

Ser Leu Leu Asp Glu Ile Lys Glu Lys Asn Gly Phe Ser Trp Tyr Arg
             20                  25                  30

Asn Leu Arg Arg Leu Gln Trp Val Trp Gln Gly Val Asp Pro Ile Glu
         35                  40                  45

Gln Glu Gln Val Leu Ala Arg Ile Ala Ser Ser Lys His Ser Arg Thr
     50                  55                  60

Asp Glu Gln Trp Leu Asp Thr Val Met Gly Tyr His Ser Gly Asn Trp
 65                  70                  75                  80

Ala Tyr Glu Trp Thr Arg Leu Gly Met Glu His Gln Lys Arg Ala Gly
                 85                  90                  95

Glu Met Thr Asn Glu Ala Ala Ser Glu Ala Leu Phe Ser Ala Ser Leu
            100                 105                 110

Ala Tyr Ser Ile Ala Gly Tyr Pro His Leu Lys Ser Asp Asn Leu Ala
        115                 120                 125

Ile Gln Ala Gln Val Leu Ala Asn Ser Ala Tyr Leu Glu Ala Ala Lys
    130                 135                 140

Lys Ser Lys Tyr Ile Ile Lys Gln Leu Glu Ile Pro Phe Glu Lys Gly
145                 150                 155                 160

Lys Ile Thr Ala His Leu His Leu Thr Asn Thr Asp Lys Pro His Pro
                165                 170                 175

Val Val Ile Val Ser Ala Gly Leu Asp Ser Leu Gln Thr Asp Met Trp
            180                 185                 190

Arg Leu Phe Arg Asp His Leu Ala Lys His Asp Ile Ala Met Leu Thr
        195                 200                 205

Val Asp Met Pro Ser Val Gly Tyr Ser Ser Lys Tyr Pro Leu Thr Glu
    210                 215                 220

Asp Tyr Ser Arg Leu His Gln Ala Val Leu Asn Glu Leu Phe Ser Ile
225                 230                 235                 240

Pro Tyr Val Asp His His Arg Val Gly Leu Ile Gly Phe Arg Phe Gly
                245                 250                 255

Gly Asn Ala Met Val Arg Leu Ser Phe Leu Glu Gln Glu Arg Ile Lys
            260                 265                 270

Ala Cys Val Ile Leu Gly Ala Pro Ile His Asp Ile Phe Ala Ser Pro
        275                 280                 285

Gln Lys Leu Gln Gln Met Pro Lys Met Tyr Leu Asp Val Leu Ala Ser
    290                 295                 300

Arg Leu Gly Lys Ser Val Val Asp Ile Tyr Ser Leu Ser Gly Gln Met
305                 310                 315                 320

Ala Ala Trp Ser Leu Lys Val Gln Gly Phe Leu Ser Ser Arg Lys Thr
                325                 330                 335

Lys Val Pro Ile Leu Ala Met Ser Leu Glu Gly Asp Pro Val Ser Pro
            340                 345                 350

Tyr Ser Asp Asn Gln Met Val Ala Phe Phe Ser Thr Tyr Gly Lys Ala
```

```
        355                 360                 365

Lys Lys Ile Ser Ser Lys Thr Ile Thr Gln Gly Tyr Glu Gln Ser Leu
    370                 375                 380

Asp Leu Ala Ile Lys Trp Leu Glu Asp Glu Leu Leu Arg
385                 390                 395


<210> SEQ ID NO 9
<211> LENGTH: 32
<212> TYPE: DNA
<213> ORGANISM: Artificial Sequence
<220> FEATURE:
<223> OTHER INFORMATION: Synthesized Primer

<400> SEQUENCE: 9

ggggtacccc gaatatgtca gaagaagtca gc                                   32


<210> SEQ ID NO 10
<211> LENGTH: 35
<212> TYPE: DNA
<213> ORGANISM: Artificial Sequence
<220> FEATURE:
<223> OTHER INFORMATION: Synthesized Primer

<400> SEQUENCE: 10

cccaagcttg tcaccttaag agttcatctt ccagc                                35


<210> SEQ ID NO 11
<211> LENGTH: 28
<212> TYPE: DNA
<213> ORGANISM: Artificial Sequence
<220> FEATURE:
<223> OTHER INFORMATION: Synthesized Primer

<400> SEQUENCE: 11

cgggatccat gacacaggca aacctgag                                        28


<210> SEQ ID NO 12
<211> LENGTH: 29
<212> TYPE: DNA
<213> ORGANISM: Artificial Sequence
<220> FEATURE:
<223> OTHER INFORMATION: Synthesized Primer

<400> SEQUENCE: 12

cccaagcttg ctatctcctg ttgtgatgc                                       29


<210> SEQ ID NO 13
<211> LENGTH: 29
<212> TYPE: DNA
<213> ORGANISM: Artificial Sequence
<220> FEATURE:
<223> OTHER INFORMATION: Synthesized Primer

<400> SEQUENCE: 13

cgggatccga cacaatgggt ctgtttgac                                       29


<210> SEQ ID NO 14
<211> LENGTH: 29
<212> TYPE: DNA
<213> ORGANISM: Artificial Sequence
<220> FEATURE:
<223> OTHER INFORMATION: Synthesized Primer

<400> SEQUENCE: 14

aactgcagta gtaattactt agttacgcg                                       29
```

<210> SEQ ID NO 15
<211> LENGTH: 30
<212> TYPE: DNA
<213> ORGANISM: Artificial Sequence
<220> FEATURE:
<223> OTHER INFORMATION: Synthesized Primer

<400> SEQUENCE: 15
gtaacctgcg atgctgtaag ccaaggatgc 30

<210> SEQ ID NO 16
<211> LENGTH: 30
<212> TYPE: DNA
<213> ORGANISM: Artificial Sequence
<220> FEATURE:
<223> OTHER INFORMATION: Synthesized Primer

<400> SEQUENCE: 16
gcatccttgg cttacagcat cgcaggttac 30

<210> SEQ ID NO 17
<211> LENGTH: 37
<212> TYPE: DNA
<213> ORGANISM: Artificial Sequence
<220> FEATURE:
<223> OTHER INFORMATION: Synthesized Primer

<400> SEQUENCE: 17
acatgcatgc aataatcgtt tgcgcagctc gataccc 37

<210> SEQ ID NO 18
<211> LENGTH: 35
<212> TYPE: DNA
<213> ORGANISM: Artificial Sequence
<220> FEATURE:
<223> OTHER INFORMATION: Synthesized Primer

<400> SEQUENCE: 18
gctctagatc ggcatgtatt gagtcaatgc cgagg 35

<210> SEQ ID NO 19
<211> LENGTH: 35
<212> TYPE: DNA
<213> ORGANISM: Artificial Sequence
<220> FEATURE:
<223> OTHER INFORMATION: Synthesized Primer

<400> SEQUENCE: 19
gctctagaag gggatccggt ctcgccatat tcgga 35

<210> SEQ ID NO 20
<211> LENGTH: 35
<212> TYPE: DNA
<213> ORGANISM: Artificial Sequence
<220> FEATURE:
<223> OTHER INFORMATION: Synthesized Primer

<400> SEQUENCE: 20
ggactagtat ccgctcgagt gagcaacatt tggcc 35

<210> SEQ ID NO 21
<211> LENGTH: 44
<212> TYPE: DNA
<213> ORGANISM: Artificial Sequence
<220> FEATURE:

<223> OTHER INFORMATION: Synthesized Primer

<400> SEQUENCE: 21
gatcctgcag aaaggaggac aaccatgagt tatactgtcg gtac 44

<210> SEQ ID NO 22
<211> LENGTH: 30
<212> TYPE: DNA
<213> ORGANISM: Artificial Sequence
<220> FEATURE:
<223> OTHER INFORMATION: Synthesized Primer

<400> SEQUENCE: 22
gatctctaga ctagaggagc ttgttaacag 30

<210> SEQ ID NO 23
<211> LENGTH: 53
<212> TYPE: DNA
<213> ORGANISM: Artificial Sequence
<220> FEATURE:
<223> OTHER INFORMATION: Synthesized Primer

<400> SEQUENCE: 23
ggggtaccaa aggaggacaa cctagctatg gcttcttcaa ctttttatat tcc 53

<210> SEQ ID NO 24
<211> LENGTH: 32
<212> TYPE: DNA
<213> ORGANISM: Artificial Sequence
<220> FEATURE:
<223> OTHER INFORMATION: Synthesized Primer

<400> SEQUENCE: 24
cggaattctt agaaagcgct caggaagagt tc 32

<210> SEQ ID NO 25
<211> LENGTH: 46
<212> TYPE: DNA
<213> ORGANISM: Artificial Sequence
<220> FEATURE:
<223> OTHER INFORMATION: Synthesized Primer

<400> SEQUENCE: 25
aactgcagaa aggaggacaa ccccgaatat gtcagaagaa gtcagc 46

<210> SEQ ID NO 26
<211> LENGTH: 32
<212> TYPE: DNA
<213> ORGANISM: Artificial Sequence
<220> FEATURE:
<223> OTHER INFORMATION: Synthesized Primer

<400> SEQUENCE: 26
gctctagaga tttgtcacct taagagttca tc 32

<210> SEQ ID NO 27
<211> LENGTH: 49
<212> TYPE: DNA
<213> ORGANISM: Artificial Sequence
<220> FEATURE:
<223> OTHER INFORMATION: Synthesized Primer

<400> SEQUENCE: 27
ctagggatcc aaaggaggac aaccgacaca atgggtctgt ttgacaaac 49

<210> SEQ ID NO 28
<211> LENGTH: 33
<212> TYPE: DNA
<213> ORGANISM: Artificial Sequence
<220> FEATURE:
<223> OTHER INFORMATION: Synthesized Primer

<400> SEQUENCE: 28
ggggtaccgt agtaattact tagttacgcg tag 33

<210> SEQ ID NO 29
<211> LENGTH: 53
<212> TYPE: DNA
<213> ORGANISM: Artificial Sequence
<220> FEATURE:
<223> OTHER INFORMATION: Synthesized Primer

<400> SEQUENCE: 29
ggggtaccaa aggaggacaa cctagctatg gcttcttcaa ctttttatat tcc 53

<210> SEQ ID NO 30
<211> LENGTH: 32
<212> TYPE: DNA
<213> ORGANISM: Artificial Sequence
<220> FEATURE:
<223> OTHER INFORMATION: Synthesized Primer

<400> SEQUENCE: 30
cggaattctt agaaagcgct caggaagagt tc 32

<210> SEQ ID NO 31
<211> LENGTH: 51
<212> TYPE: DNA
<213> ORGANISM: Artificial Sequence
<220> FEATURE:
<223> OTHER INFORMATION: Synthesized Primer

<400> SEQUENCE: 31
aactgcagaa aggaggacaa cctagctatg gccatagaaa cctcggcatt g 51

<210> SEQ ID NO 32
<211> LENGTH: 32
<212> TYPE: DNA
<213> ORGANISM: Artificial Sequence
<220> FEATURE:
<223> OTHER INFORMATION: Synthesized Primer

<400> SEQUENCE: 32
gctctagaga tttgtcacct taagagttca tc 32

<210> SEQ ID NO 33
<211> LENGTH: 49
<212> TYPE: DNA
<213> ORGANISM: Artificial Sequence
<220> FEATURE:
<223> OTHER INFORMATION: Synthesized Primer

<400> SEQUENCE: 33
ctagggatcc aaaggaggac aaccgacaca atgggtctgt ttgacaaac 49

<210> SEQ ID NO 34
<211> LENGTH: 33
<212> TYPE: DNA
<213> ORGANISM: Artificial Sequence
<220> FEATURE:
<223> OTHER INFORMATION: Synthesized Primer

<400> SEQUENCE: 34
ggggtaccgt agtaattact tagttacgcg tag 33

<210> SEQ ID NO 35
<211> LENGTH: 53
<212> TYPE: DNA
<213> ORGANISM: Artificial Sequence
<220> FEATURE:
<223> OTHER INFORMATION: Synthesized Primer

<400> SEQUENCE: 35
ggggtaccaa aggaggacaa cctagctatg gcttcttcaa ctttttatat tcc 53

<210> SEQ ID NO 36
<211> LENGTH: 32
<212> TYPE: DNA
<213> ORGANISM: Artificial Sequence
<220> FEATURE:
<223> OTHER INFORMATION: Synthesized Primer

<400> SEQUENCE: 36
cggaattctt agaaagcgct caggaagagt tc 32

<210> SEQ ID NO 37
<211> LENGTH: 415
<212> TYPE: PRT
<213> ORGANISM: Vibrio parahaemolyticus

<400> SEQUENCE: 37

```
Met Ser Glu Glu Val Ser Lys Asn Leu Ser Glu Thr Leu Phe Ala Asn
  1               5                  10                  15

His Lys Gln Ala Lys Glu Thr Ser Glu Leu Thr Arg Tyr Met Pro Ser
             20                  25                  30

Ser Gln Ser Phe Leu Asp Glu Lys Arg Glu Ser Asp Gly Tyr Lys Trp
         35                  40                  45

Tyr Arg Asn Leu Arg Arg Met Gln Trp Thr Trp Gln Gly Leu Asp Pro
     50                  55                  60

Ile Glu Ile Glu Ala Val Leu Ala Lys Ile Ala Ala Ser Lys His Ser
 65                  70                  75                  80

Arg Thr His Glu Glu Trp Leu Asp Thr Val Met Gly Tyr His Ser Gly
                 85                  90                  95

Asn Trp Thr Tyr Glu Trp Thr Lys Leu Gly Met Leu His Gln Lys Arg
            100                 105                 110

Ser Ser Gln Leu Lys Gly Glu Glu Ala Ala Asp Glu Leu Phe Asn Ala
        115                 120                 125

Ser Leu Cys Phe Ser Ile Ala Gly Tyr Pro His Leu Lys Asn Asp Asn
    130                 135                 140

Leu Ala Thr Gln Ala Gln Val Leu Ala Ser Ser Ala Tyr Thr Glu Ala
145                 150                 155                 160

Thr Lys Lys Thr Lys Tyr Ile Val Lys Arg Leu Glu Ile Pro Tyr Gln
                165                 170                 175

Lys Lys Ser Ile Ile Ala His Leu His Leu Thr Ser Thr Glu Lys Pro
            180                 185                 190

Gln Pro Val Val Ile Val Ser Ala Gly Leu Asp Ser Leu Gln Thr Asp
        195                 200                 205

Leu Trp Thr Val Phe Arg Asp His Leu Ala Lys Lys Asn Ile Ala Met
    210                 215                 220

Leu Thr Val Asp Met Pro Ser Ile Gly His Asn Thr His Trp Asn Leu
```

```
225                 230                 235                 240

Thr Glu Asp Thr Ser Val Leu His Gln Ala Val Leu Asn Glu Leu Tyr
                245                 250                 255

Ser Ile Pro Trp Val Asp His His Arg Val Gly Leu Ile Gly Phe Arg
            260                 265                 270

Phe Gly Gly Asn Ala Met Val Arg Leu Ser Phe Leu Glu Gln Asp Lys
        275                 280                 285

Ile Lys Ala Cys Val Ser Met Gly Ala Pro Ile His Asp Val Leu Ser
    290                 295                 300

Ser Pro Asp Lys Leu Lys Ser Met Pro Lys Met Tyr Leu Asp Val Leu
305                 310                 315                 320

Ala Ser Arg Leu Gly Lys Asn Ala Val Asp Ile His Ser Leu Ser Ser
                325                 330                 335

Gln Leu Met Ala Trp Ser Leu Lys Val Gln Gly Ile Leu Ser Ser Arg
            340                 345                 350

Lys Thr Arg Val Pro Ile Leu Ala Met Ser Leu Glu Gly Asp Pro Val
        355                 360                 365

Ser Pro Tyr Ser Asp Asn Gln Met Val Ala Leu Tyr Ser Asp Tyr Gly
    370                 375                 380

Lys Ala Lys Lys Ile Ser Ala Lys Thr Ile Thr Gln Gly Tyr Glu Gln
385                 390                 395                 400

Ser Leu Asp Leu Ala Ile Lys Trp Leu Glu Asp Glu Leu Met Arg
                405                 410                 415


<210> SEQ ID NO 38
<211> LENGTH: 415
<212> TYPE: PRT
<213> ORGANISM: Vibrio cholerae

<400> SEQUENCE: 38

Met Ser Glu Ala Ser Ser Lys Asn Leu Ser Glu Thr Leu Phe Gln Asn
  1               5                  10                  15

His Lys Gln Ala Lys Glu Thr Ser Ser Leu Thr Gln Tyr Met Pro Ser
             20                  25                  30

Ser Leu Glu Leu Leu Asp Thr Arg Arg Glu Gln Ser Ser Gln Ala Trp
         35                  40                  45

Tyr Arg Asn Leu Arg Arg Leu Gln Trp Ile Trp Gln Gly Val Asp Pro
     50                  55                  60

Val Glu Gln Glu Glu Ile Leu Ala Arg Ile Ala Ser Ser Lys His Ser
 65                  70                  75                  80

Arg Thr His Asp Glu Trp Leu Asp Thr Val Met Gly Tyr Arg Ser Gly
                 85                  90                  95

Asn Trp Thr Tyr Glu Trp Thr Arg Val Gly Met Leu His Gln Lys Gln
            100                 105                 110

Ala Ala Glu Arg Gln Gly Glu Glu Ala Ala Asp Gln Met Phe Ala Ala
        115                 120                 125

Ala Leu Tyr Tyr Ser Ile Ala Gly Tyr Pro His Leu Arg Asn Asp Asn
    130                 135                 140

Leu Ala Leu Gln Ala Gln Val Leu Ala Asn Asn Ala Tyr Gln Glu Ala
145                 150                 155                 160

Ala Lys Leu Thr Gly Phe Val Val Lys Arg Leu Glu Phe Ser Tyr Gln
                165                 170                 175

Asn Lys Lys Ile Ala Gly Tyr Leu His Leu Arg Asn Thr Asp Ser Pro
            180                 185                 190
```

```
Lys Pro Val Val Leu Val Ser Ala Gly Leu Asp Ser Leu Gln Thr Asp
        195                 200                 205

Met Trp Arg Leu Phe Arg Asp Tyr Leu Ala Lys Arg Asp Ile Ala Met
    210                 215                 220

Leu Thr Ile Asp Met Pro Ser Leu Gly Ala Ser Ser His Trp Pro Leu
225                 230                 235                 240

Thr Glu Asp Ser Ser Cys Leu His Gln Ala Val Leu Asn Gln Leu Ala
                245                 250                 255

Asp Leu Pro Trp Val Asp His Phe Arg Ile Gly Leu Ile Gly Phe Arg
            260                 265                 270

Phe Gly Gly Asn Ala Met Ala Arg Leu Ala Phe Leu Glu Ser Asp Lys
        275                 280                 285

Val Lys Ala Cys Val Ser Leu Gly Ala Pro Ile His Asp Ile Phe Thr
    290                 295                 300

Ser Pro Asn Lys Leu Ala Ala Met Pro Lys Met Tyr Leu Asp Val Leu
305                 310                 315                 320

Ala Ser Arg Leu Gly Lys Asn Val Val Asp Val Arg Ser Leu Ser Gly
                325                 330                 335

Gln Leu Met Ala Trp Ser Leu Lys Val Gln Gly Phe Met Ser Gly Arg
            340                 345                 350

Arg Thr Lys Thr Pro Ile Leu Ala Leu Gly Leu Glu Gly Asp Pro Val
        355                 360                 365

Ser Pro Tyr Ser Asp Asn Gln Leu Val Ala Leu Phe Ser Gln Gly Gly
    370                 375                 380

Gln Ala Lys Lys Val Lys Ser Lys Thr Ile Ser Gln Gly Tyr Glu Gln
385                 390                 395                 400

Ser Leu Asp Leu Ala Ile Asn Trp Leu Glu Asp Glu Leu Cys Lys
                405                 410                 415


<210> SEQ ID NO 39
<211> LENGTH: 414
<212> TYPE: PRT
<213> ORGANISM: Escherichia coli

<400> SEQUENCE: 39

Met Thr Gln Ala Asn Leu Ser Glu Thr Leu Phe Lys Pro Arg Phe Lys
  1               5                  10                  15

His Pro Glu Thr Ser Thr Leu Val Arg Arg Phe Asn His Gly Ala Gln
             20                  25                  30

Pro Pro Val Gln Ser Ala Leu Asp Gly Lys Thr Ile Pro His Trp Tyr
         35                  40                  45

Arg Met Ile Asn Arg Leu Met Trp Ile Trp Arg Gly Ile Asp Pro Arg
     50                  55                  60

Glu Ile Leu Asp Val Gln Ala Arg Ile Val Met Ser Asp Ala Glu Arg
 65                  70                  75                  80

Thr Asp Asp Asp Leu Tyr Asp Thr Val Ile Gly Tyr Arg Gly Gly Asn
                 85                  90                  95

Trp Ile Tyr Glu Trp Ala Thr Gln Ala Met Val Trp Gln Gln Lys Ala
            100                 105                 110

Cys Ala Glu Asp Asp Pro Gln Leu Ser Gly Arg His Trp Leu His Ala
        115                 120                 125

Ala Thr Leu Tyr Asn Ile Ala Ala Tyr Pro His Leu Lys Gly Asp Asp
    130                 135                 140

Leu Ala Glu Gln Ala Gln Ala Leu Ser Asn Arg Ala Tyr Glu Glu Ala
145                 150                 155                 160
```

```
Ala Gln Arg Leu Pro Gly Thr Met Arg Gln Met Glu Phe Thr Val Pro
                165                 170                 175

Gly Gly Ala Pro Ile Thr Gly Phe Leu His Met Pro Lys Gly Asp Gly
            180                 185                 190

Pro Phe Pro Thr Val Leu Met Cys Gly Gly Leu Asp Ala Met Gln Thr
        195                 200                 205

Asp Tyr Tyr Ser Leu Tyr Glu Arg Tyr Phe Ala Pro Arg Gly Ile Ala
    210                 215                 220

Met Leu Thr Ile Asp Met Pro Ser Val Gly Phe Ser Ser Lys Trp Lys
225                 230                 235                 240

Leu Thr Gln Asp Ser Ser Leu Leu His Gln His Val Leu Lys Ala Leu
                245                 250                 255

Pro Asn Val Pro Trp Val Asp His Thr Arg Val Ala Ala Phe Gly Phe
            260                 265                 270

Arg Phe Gly Ala Asn Val Ala Val Arg Leu Ala Tyr Leu Glu Ser Pro
        275                 280                 285

Arg Leu Lys Ala Val Ala Cys Leu Gly Pro Val Val His Thr Leu Leu
    290                 295                 300

Ser Asp Phe Lys Cys Gln Gln Gln Val Pro Glu Met Tyr Leu Asp Val
305                 310                 315                 320

Leu Ala Ser Arg Leu Gly Met His Asp Ala Ser Asp Glu Ala Leu Arg
                325                 330                 335

Val Glu Leu Asn Arg Tyr Ser Leu Lys Val Gln Gly Leu Leu Gly Arg
            340                 345                 350

Arg Cys Pro Thr Pro Met Leu Ser Gly Tyr Trp Lys Asn Asp Pro Phe
        355                 360                 365

Ser Pro Glu Glu Asp Ser Arg Leu Ile Thr Ser Ser Ser Ala Asp Gly
    370                 375                 380

Lys Leu Leu Glu Ile Pro Phe Asn Pro Val Tyr Arg Asn Phe Asp Lys
385                 390                 395                 400

Gly Leu Gln Glu Ile Thr Asp Trp Ile Glu Lys Arg Leu Cys
                405                 410


<210> SEQ ID NO 40
<211> LENGTH: 414
<212> TYPE: PRT
<213> ORGANISM: Shigella flexneri

<400> SEQUENCE: 40

Met Thr Gln Ala Asn Leu Ser Glu Thr Leu Phe Lys Pro Arg Phe Lys
  1               5                  10                  15

His Pro Glu Thr Ser Thr Leu Val Arg Arg Phe Asn His Gly Ala Gln
             20                  25                  30

Pro Pro Val Gln Ser Ala Leu Asp Gly Lys Thr Ile Pro His Trp Tyr
         35                  40                  45

Arg Met Ile Asn Arg Leu Met Trp Ile Trp Arg Gly Ile Asp Pro Arg
     50                  55                  60

Glu Ile Leu Asp Val Gln Ala Arg Ile Val Met Ser Asp Ala Glu Arg
 65                  70                  75                  80

Thr Asp Asp Asp Leu Tyr Asp Thr Val Ile Gly Tyr Arg Gly Gly Asn
                 85                  90                  95

Trp Ile Tyr Glu Trp Ala Thr Gln Ala Met Val Trp Gln Gln Lys Ala
            100                 105                 110

Cys Thr Glu Glu Asp Pro Gln Leu Ser Gly Arg His Trp Leu His Ala
```

```
        115                 120                 125

Ala Thr Leu Tyr Asn Ile Ala Ala Tyr Pro His Leu Lys Gly Asp Asp
    130                 135                 140

Leu Ala Glu Gln Ala Gln Ala Leu Ser Asn Arg Ala Tyr Glu Glu Ala
145                 150                 155                 160

Ala Gln Arg Leu Pro Gly Thr Met Arg Gln Met Glu Phe Thr Val Pro
                165                 170                 175

Gly Gly Ala Pro Ile Thr Gly Phe Leu His Met Pro Lys Gly Asp Gly
            180                 185                 190

Pro Phe Pro Thr Val Leu Met Cys Gly Gly Leu Asp Ala Met Gln Thr
        195                 200                 205

Asp Tyr Tyr Ser Leu Tyr Glu Arg Tyr Phe Ala Pro Arg Gly Ile Ala
    210                 215                 220

Met Leu Thr Ile Asp Met Pro Ser Val Gly Phe Ser Ser Lys Trp Lys
225                 230                 235                 240

Leu Thr Gln Asp Ser Ser Leu Leu His Gln His Val Leu Lys Ala Leu
                245                 250                 255

Pro Asn Val Pro Trp Val Asp His Thr Arg Val Ala Ala Phe Gly Phe
            260                 265                 270

Arg Phe Gly Ala Asn Val Ala Val Arg Leu Ala Tyr Leu Glu Ser Pro
        275                 280                 285

Arg Leu Lys Ala Val Ala Cys Leu Gly Pro Val Val His Thr Leu Leu
    290                 295                 300

Ser Asp Phe Lys Cys Gln Gln Gln Val Pro Glu Met Tyr Leu Asp Val
305                 310                 315                 320

Leu Ala Ser Arg Leu Gly Met His Asp Ala Ser Asp Glu Ala Leu Arg
                325                 330                 335

Val Glu Leu Asn Arg Tyr Ser Leu Lys Val Gln Gly Leu Leu Gly Arg
            340                 345                 350

Arg Cys Pro Thr Pro Met Leu Ser Gly Tyr Trp Lys Asn Asp Pro Phe
        355                 360                 365

Ser Pro Glu Glu Asp Ser Arg Leu Ile Thr Ser Ser Ser Ala Asp Gly
    370                 375                 380

Lys Leu Leu Glu Ile Pro Phe Asn Pro Val Tyr Arg Asn Phe Asp Lys
385                 390                 395                 400

Gly Leu Gln Glu Ile Thr Gly Trp Ile Glu Lys Arg Leu Cys
                405                 410


<210> SEQ ID NO 41
<211> LENGTH: 414
<212> TYPE: PRT
<213> ORGANISM: Salmonella enterica

<400> SEQUENCE: 41

Met Thr Gln Ala Asn Leu Ser Glu Thr Leu Phe Lys Pro Arg Phe Lys
  1               5                  10                  15

His Thr Glu Thr Ser Ala Leu Val Arg Arg Phe Asn Arg Gly Ser Gln
             20                  25                  30

Pro Pro Met Gln Ser Ala Leu Asp Gly Lys Asn Val Pro His Trp Tyr
         35                  40                  45

Arg Met Ile Asn Arg Leu Met Trp Ile Trp Arg Gly Val Asp Pro Arg
     50                  55                  60

Glu Ile Leu Asp Val Gln Ala Arg Ile Val Met Ser Asp Ala Glu Arg
 65                  70                  75                  80
```

```
Thr Asp Asp Asp Leu Tyr Asp Thr Val Ile Gly Tyr Arg Gly Gly Asn
                 85                  90                  95

Trp Ile Tyr Glu Trp Ala Lys Gln Ala Met Asp Trp Gln Gln Lys Ala
            100                 105                 110

Cys Gln Glu Gln Asp Ala Met Arg Ser Gly Arg Tyr Trp Leu His Ala
        115                 120                 125

Ser Thr Leu Tyr Asn Ile Ala Ala Tyr Pro His Leu Lys Gly Asp Glu
    130                 135                 140

Leu Ala Glu Gln Ala Gln Ala Leu Ala Asn Arg Ala Tyr Glu Glu Ala
145                 150                 155                 160

Ala Gln Arg Leu Pro Gly Ser Leu Arg Glu Met Glu Phe Ala Val Pro
                165                 170                 175

Gly Gly Ser Pro Val Thr Ala Phe Leu His Met Pro Lys Gly Asp Gly
            180                 185                 190

Pro Phe Pro Thr Val Leu Met Cys Gly Gly Leu Asp Ala Met Gln Thr
        195                 200                 205

Asp Tyr Tyr Thr Leu Tyr Glu Arg Tyr Leu Ala Pro Arg Gly Ile Ala
    210                 215                 220

Met Leu Thr Leu Asp Met Pro Ser Val Gly Phe Ser Ser Lys Trp Lys
225                 230                 235                 240

Leu Thr Gln Asp Ser Ser Leu Ile His Gln His Val Leu Lys Ala Leu
                245                 250                 255

Thr Asn Val Pro Trp Val Asp His Thr Arg Val Ala Ala Phe Gly Phe
            260                 265                 270

Arg Phe Gly Ala Asn Val Ala Val Arg Leu Ala Tyr Leu Glu Ala Pro
        275                 280                 285

Arg Leu Lys Ala Val Ala Cys Leu Gly Pro Val Val His Ala Leu Leu
    290                 295                 300

Ser Asp Pro Gln Arg Gln Ser Thr Val Pro Glu Met Tyr Leu Asp Val
305                 310                 315                 320

Leu Ala Ser Arg Leu Gly Met His Asp Ala Ser Asp Glu Ala Leu Arg
                325                 330                 335

Val Glu Leu Asn Arg Tyr Ser Leu Lys Val Gln Gly Leu Leu Gly Arg
            340                 345                 350

Arg Cys Pro Thr Pro Met Leu Ser Gly Phe Trp Lys Asn Asp Pro Phe
        355                 360                 365

Ser Pro Glu Asp Glu Ser Arg Leu Ile Thr Ser Ser Ser Ser Asp Gly
    370                 375                 380

Lys Leu Ile Glu Ile Pro Phe Asn Pro Val Tyr Arg Asn Phe Asp Lys
385                 390                 395                 400

Ala Leu Gln Glu Ile Thr Asp Trp Ile His His Arg Leu Cys
                405                 410
```

<210> SEQ ID NO 42
<211> LENGTH: 421
<212> TYPE: PRT
<213> ORGANISM: Yersinia pestis

<400> SEQUENCE: 42

```
Met Glu Ala Thr Val Thr Met Ala Gln Ala Asn Leu Ser Glu Ile Leu
  1               5                  10                  15

Phe Lys Pro Lys Phe Lys His Pro Glu Thr Ser Thr Leu Val Arg Arg
             20                  25                  30

Thr His Cys Asn His Val Val Asn Ile His Ser Ala Leu Asp Gly Asp
         35                  40                  45
```

-continued

```
Thr Ala Asn His Trp Tyr Arg Met Ile Asn Arg Leu Met Trp Thr Trp
     50                  55                  60

Arg Gly Ile Asp Pro Leu Glu Ile Glu Glu Val Leu Ser Arg Ile Ala
 65                  70                  75                  80

Cys Ser Lys Ala Glu His Ser Asn Asn Glu Leu Leu Asp Thr Val Val
                 85                  90                  95

Gly Tyr Arg Asn Gly Asn Trp Ile Tyr Glu Trp Ala Asn Gln Gly Met
            100                 105                 110

Met Trp Gln Gln Lys Ala Met Glu Glu Thr Asp Pro Gly Ser Ala Gly
        115                 120                 125

Gln Phe Trp Leu Asn Ala Ala Asn Leu Tyr Ser Ile Ala Ser Tyr Pro
    130                 135                 140

His Leu Lys Gly Asp Glu Leu Ser Glu Gln Ala Glu Val Leu Ser Asn
145                 150                 155                 160

Arg Ala Tyr Glu Glu Ala Ala Lys Tyr Leu Pro Tyr Thr Leu Lys Glu
                165                 170                 175

Leu Thr Phe Pro Ile Ser Asp Gly Gly Ser Leu Ser Gly Phe Leu His
            180                 185                 190

Met Pro Thr Val Gly Ser Ala Pro Phe Pro Thr Val Leu Met Cys Gly
        195                 200                 205

Gly Leu Asp Thr Leu Gln Ser Asp Tyr His Arg Leu Phe Arg Asp Tyr
    210                 215                 220

Leu Glu Pro Lys Gly Ile Ala Met Leu Thr Ile Asp Leu Pro Ser Val
225                 230                 235                 240

Gly Ala Ser Ser Arg Trp Lys Leu Thr Gln Asp Thr Ser Tyr Leu His
                245                 250                 255

Gln Gln Val Leu Gln Ala Leu Ala Asp Val Pro Trp Val Asp His Gln
            260                 265                 270

Arg Val Ser Val Phe Gly Phe Arg Phe Gly Ala Asn Val Ala Val Arg
        275                 280                 285

Leu Gly Tyr Leu Glu Pro Gln Arg Val Arg Ala Val Ala Cys Leu Gly
    290                 295                 300

Pro Ile Val His His Leu Leu Cys Asn Ser Asp Ser Leu Arg Lys Val
305                 310                 315                 320

Pro Asp Met Tyr Met Asp Val Met Ala Ser Arg Leu Gly Met Ala Asp
                325                 330                 335

Ser Thr Asp Glu Thr Leu Asn Thr Glu Met Asn Arg Tyr Ser Leu Lys
            340                 345                 350

Thr Gln Gly Leu Leu Gly Arg Arg Cys Gln Thr Pro Met Leu Ala Gly
        355                 360                 365

Phe Trp Glu Asn Asp Pro Phe Ser Pro Lys Glu Glu Ala Lys Leu Ile
    370                 375                 380

Cys Ser Ser Ser Ala Asp Gly Lys Leu Leu Ala Ile Pro Ser Lys Pro
385                 390                 395                 400

Leu Tyr Glu Asn Phe His Arg Ala Leu Leu Gln Thr Ser Glu Trp Leu
                405                 410                 415

Glu Asp Lys Met Arg
            420
```